United States Patent [19]
Kaji et al.

[11] Patent Number: 6,126,633
[45] Date of Patent: Oct. 3, 2000

[54] SURGICAL INSTRUMENT

[75] Inventors: Kunihide Kaji, Hachioji; Tsuyoshi Tsukagoshi, Fuchu, both of Japan

[73] Assignee: Olympus Optical Co., Ltd., Tokyo, Japan

[21] Appl. No.: 09/111,198

[22] Filed: Jul. 7, 1998

[30]  Foreign Application Priority Data

Jul. 11, 1997 [JP] Japan ..................... 9-186200
Jun. 16, 1998 [JP] Japan ..................... 10-168246

[51] Int. Cl.⁷ .................................. A61M 37/00
[52] U.S. Cl. ................. 604/95.04; 604/528; 604/164.01
[58] Field of Search ................... 604/95, 264, 19, 604/528, 48, 523, 164.01; 600/138–142, 146–151, 156

[56] References Cited

U.S. PATENT DOCUMENTS 4,911,148  3/1990  Sosnowski et al. ................ 128/6
5,167,645 12/1992  Castillo .
5,389,090  2/1995  Fischell et al. .
5,599,305  2/1997  Hermann et al. ................. 604/95

FOREIGN PATENT DOCUMENTS 62-253079 11/1987 Japan .
5-21587    3/1993 Japan .
5-253178  10/1993 Japan .
5-253179  10/1993 Japan .
5-253298  10/1993 Japan .
5-261062  10/1993 Japan .
5-261063  10/1993 Japan .

*Primary Examiner*—Wynn Wood Coggins
*Assistant Examiner*—Deborah Blyvers
*Attorney, Agent, or Firm*—Frishauf, Holtz, Goodman, Langer & Chick, P.C.

[57]  ABSTRACT

An elongate injection needle is passed through an applicator. When the needle is inserted into any desired insertion position, it is fixed to the applicator by means of an instrument fixing member of a handle section. In this state, the shape of a bendable portion on the distal end side of an insert section can be easily changed by turning one of two knobs of the handle section to bend the bendable portion.

24 Claims, 14 Drawing Sheets

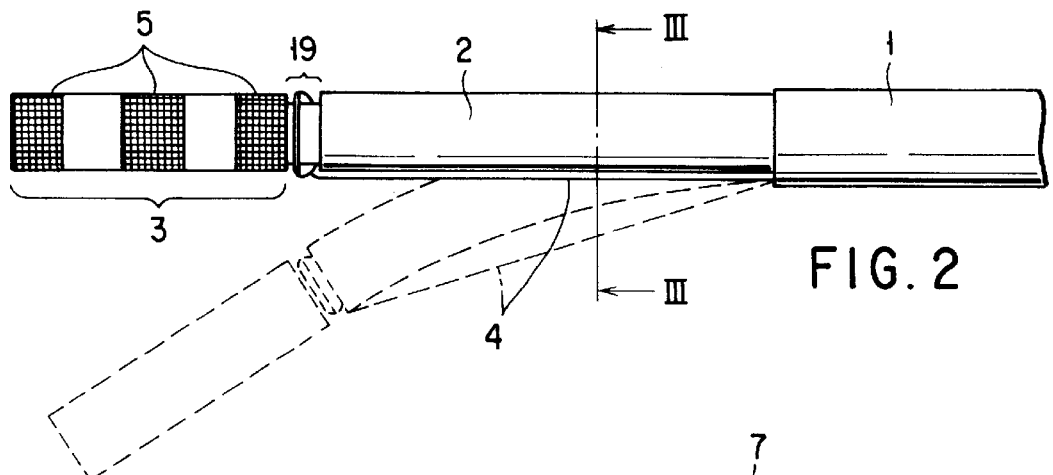
FIG. 2
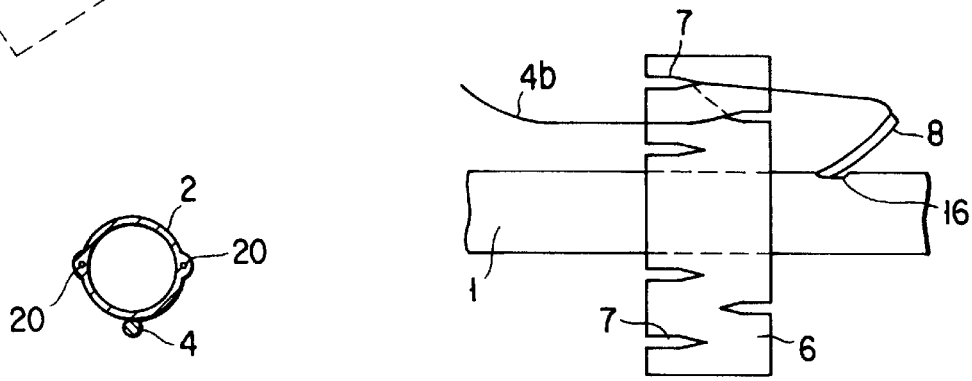
FIG. 3
FIG. 4
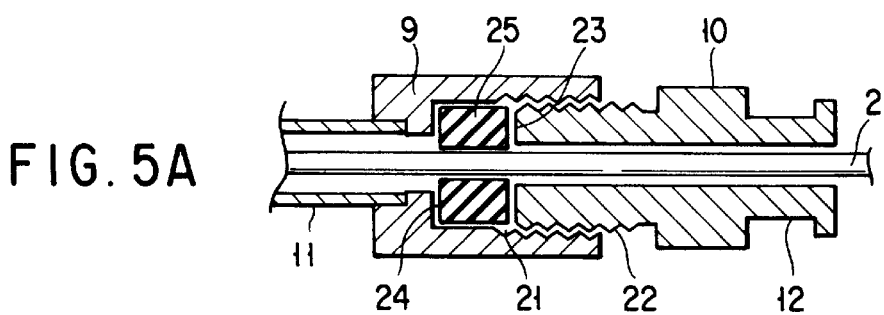
FIG. 5A
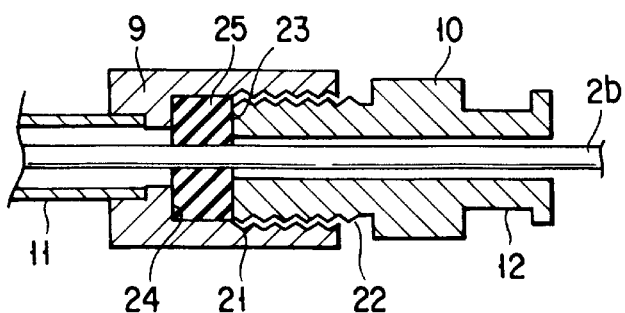
FIG. 5B

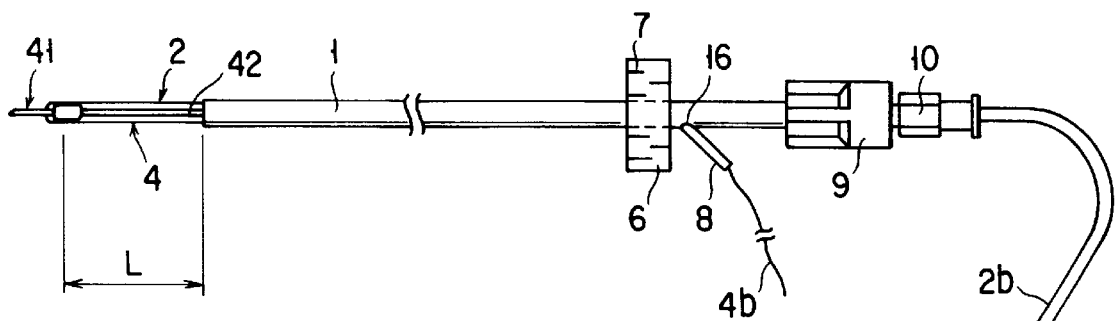
FIG. 9
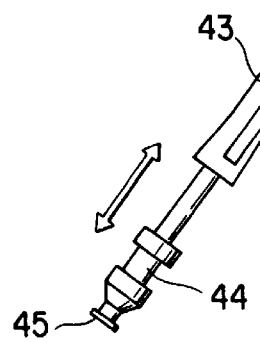
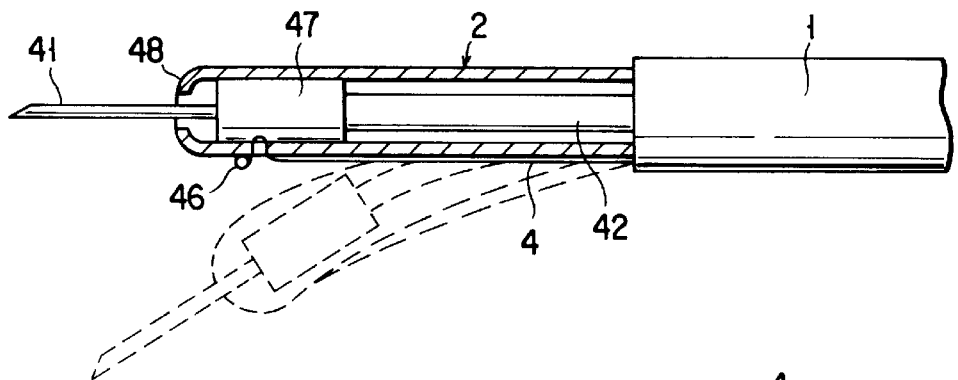
FIG. 10A
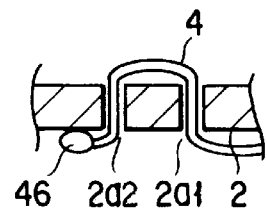
FIG. 10B

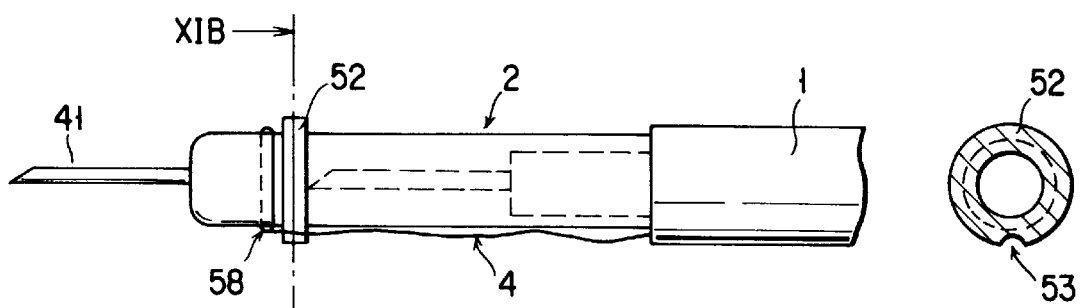
FIG. 11A
FIG. 11B
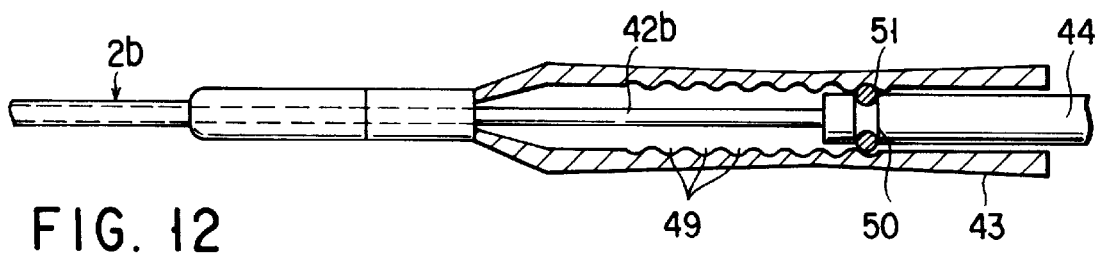
FIG. 12
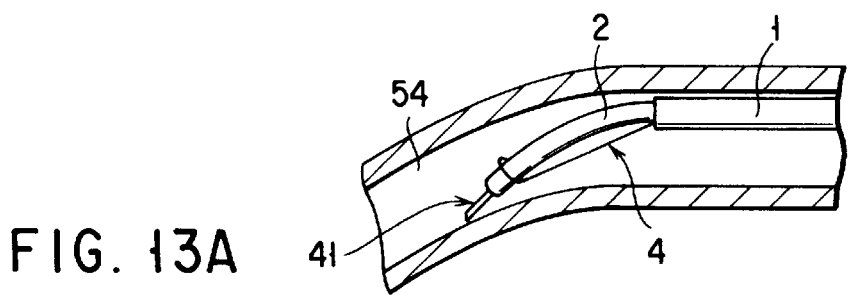
FIG. 13A
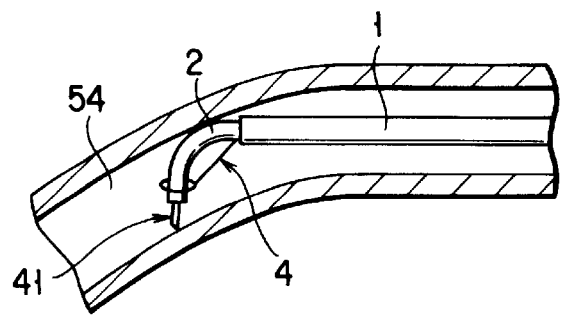
FIG. 13B

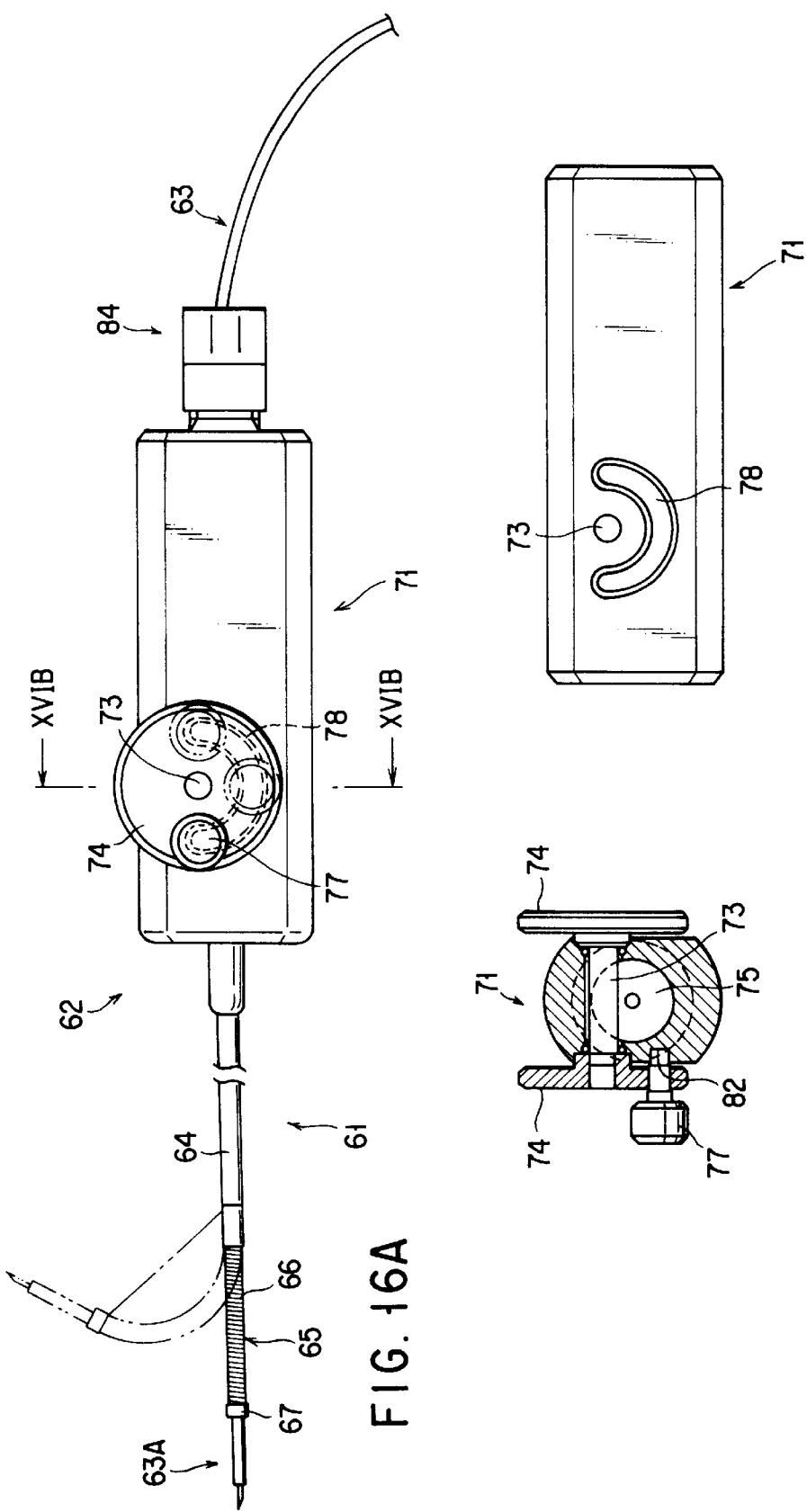

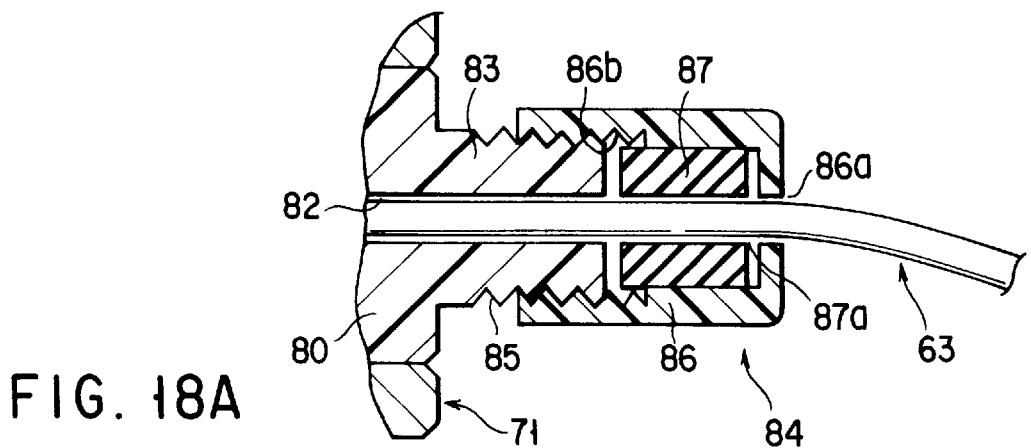
FIG. 18A
FIG. 18B
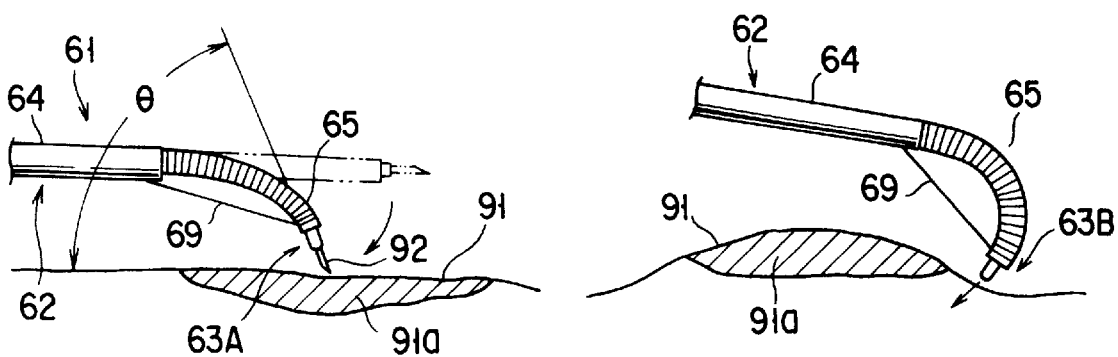
FIG. 19A FIG. 19B

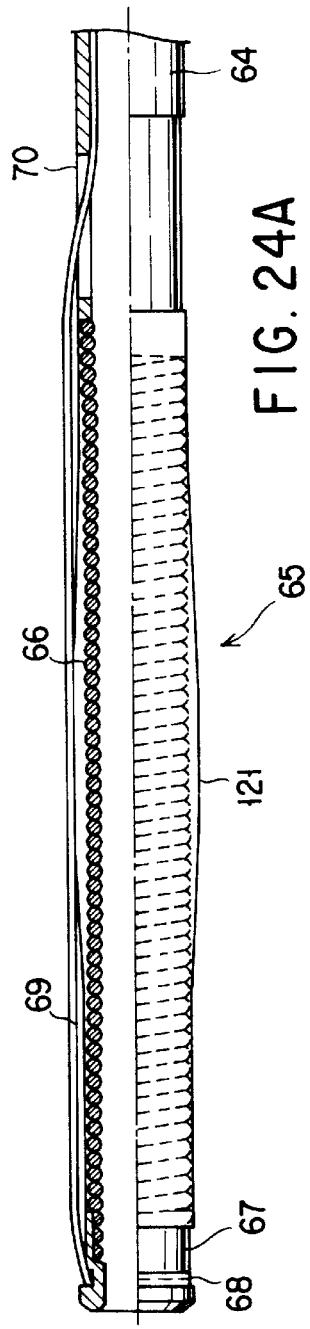
FIG. 24A
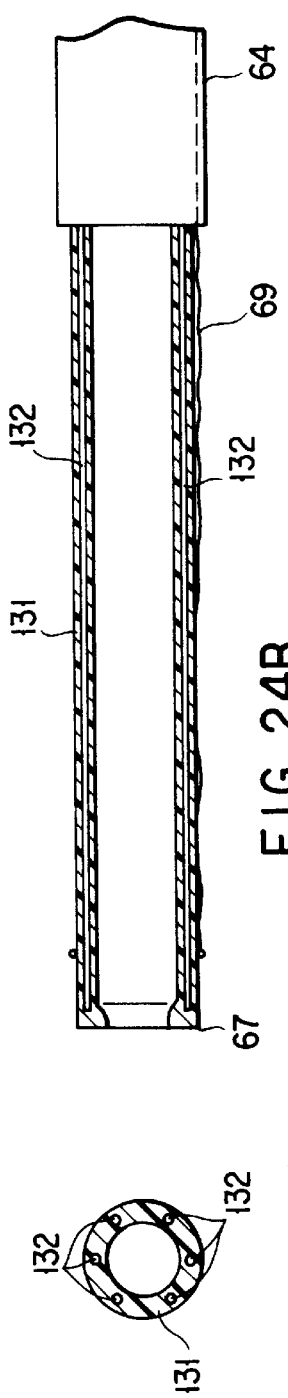
FIG. 24B
FIG. 24C
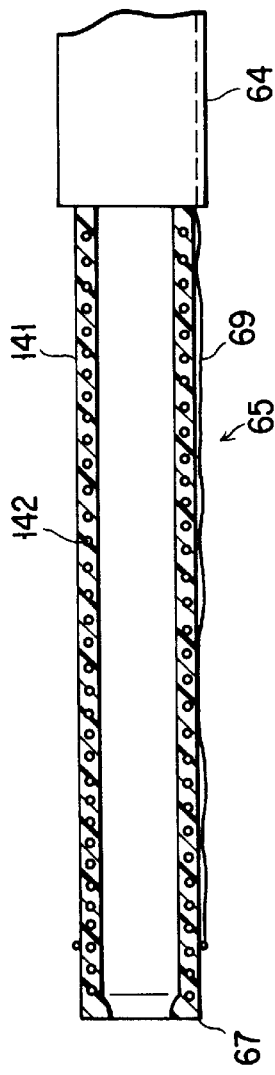
FIG. 24D

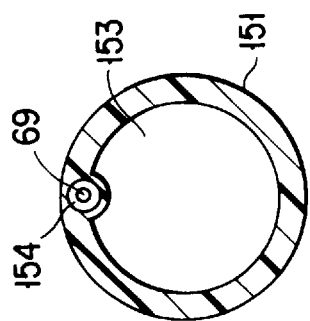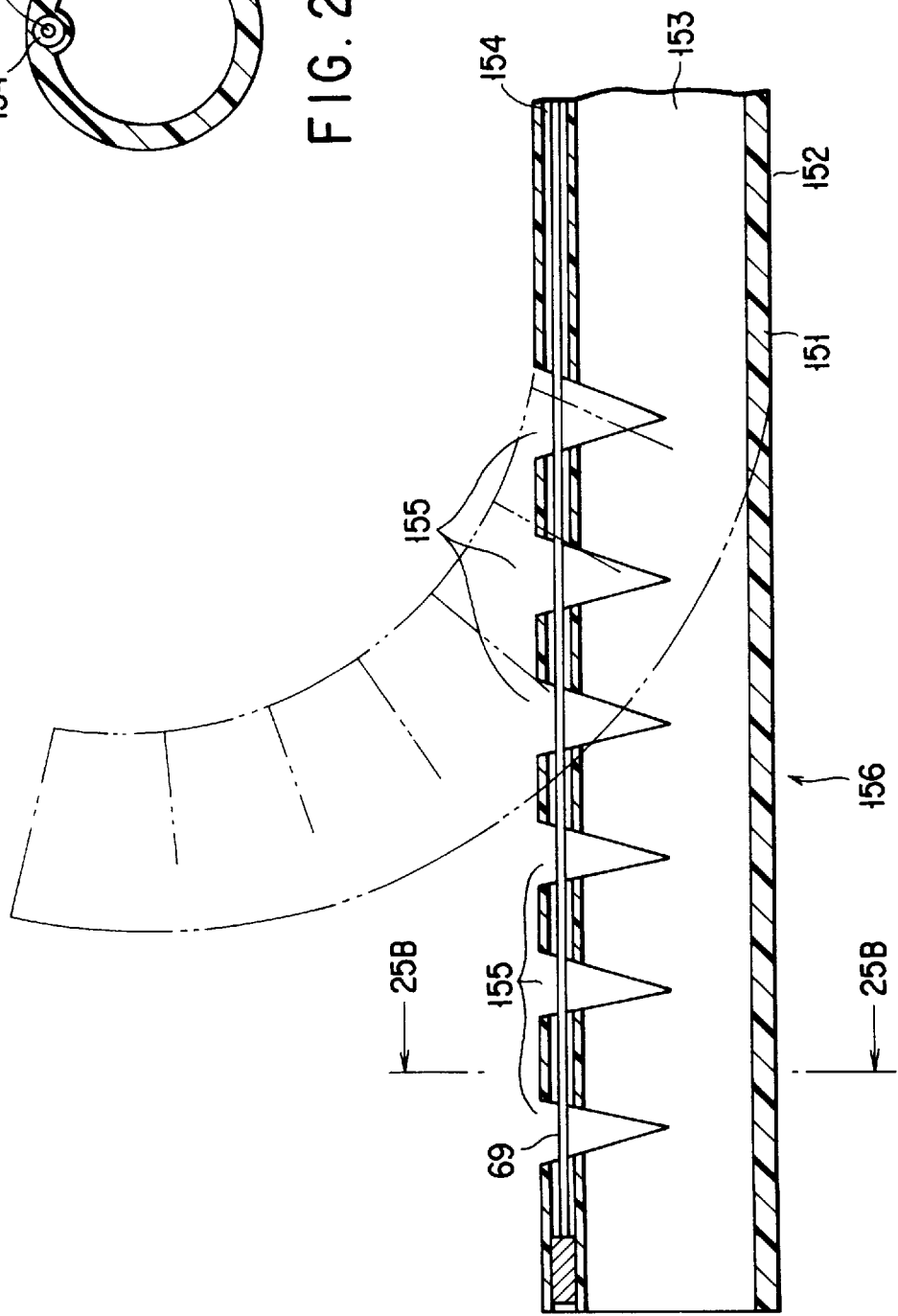

SURGICAL INSTRUMENT

BACKGROUND OF THE INVENTION

The present invention relates to a surgical instrument used in an endoscopic surgical operation.

Endoscopic surgical operations are conducted extensively these days. In these operations, endoscopic images that are displayed on a monitor are observed as treatment is carried out. An instrument used in the treatment has an axis that is long enough for extracorporeal manipulation.

In general, the instrument of this type is passed through a cylindrical member, called a trocar, which connects the interior of a patient's body and the outside. Since the trocar is fixed in its entrance position, in this case, the instrument and an organism as an object of treatment are not always in desirable relative positions. Thus, manipulating the instrument requires technical skill of a user.

The manipulation of the instrument is difficult in the case where the instrument is held extending in the direction of the tangent to the plane of an organism as a to-be-treated object or where the viewing direction of an endoscope is close to the axial direction of the instrument, in particular.

In excising only a mucomembranous structure of the stomach or intestine under observation through an endoscope, as a specific example, a medical solution is locally injected into a submucosa by means of a injection needle. If the injection needle is located so that its central axis extends in the direction of the tangent to the plane of the target mucomembranous structure, in doing this, it is difficult to thrust the needle deep into the mucomembranous structure. In this case, therefore, the medical solution cannot be easily injected to an appropriate depth in the mucomembranous structure.

In the case of biopsy, moreover, an organism is partially excised and recovered by means of a cup-shaped forceps, called a bioptome, having a sharp edge. If the plane of the organism and the central axis of the forceps are substantially parallel to each other, also in this case, the organism cannot be excised satisfactorily.

Described in Jpn. Pat. Appln. KOKAI Publication Nos. 5-253178, 5-253179 and 5-253298 are instruments that have been developed to solve these problems. These instruments are provided with a bending device for bending a injection needle on the handling side, whereby the needle can be thrust squarely into a target organism.

Described in Jpn. Pat. Appln. KOKAI Publication No. 5-261062, moreover, is an instrument in-which the tip portion of a injection needle is formed of a shape-memory alloy, and needling is facilitated by using means for remotely heating the needle tip portion. According to an arrangement disclosed in Jpn. Pat. Appln. KOKAI Publication No. 8-332189, furthermore, an area near the distal end portion of a bioptome is bendable in any desired direction.

In conducting cholangiography in the course of laparoscopic cholecystectomy, another difficulty is found in inserting a catheter to inject a contrast medium via the cystic duct. In a typical method of contrast medium injection for this technique, a soft tub called a contrast catheter is held by means of a forceps as it is guided to and inserted into an incision region in the cystic duct. During this treatment, the central axis of the catheter is not always in line with the extending direction of the cystic duct. Even after the catheter tube is inserted into the incision region with success, moreover, it is liable to be caught by a valve in the cystic duct. Thus, the catheter cannot be inserted deep into the duct.

Described in U.S. Pat. No. 5,167,645 is an instrument in which a bent portion is attached to the distal end of a bile-duct catheter in order to solve these problems. According to an arrangement described in U.S. Pat. No. 5,389,090, furthermore, the efficiency of insertion is improved by using a hollow tube that is previously made highly susceptible to bending.

In any of the cases described above, the central axis of the distal end portion is inclined at a certain angle to that of the instrument, in order to improve the direction of approach of the instrument to the target organism.

According to the aforementioned conventional injection needle with the bendable tip, however, the degree of its curvature cannot be changed although its curved shape is variable. In the case where an endoscope and the needle are arranged substantially coaxially, therefore, the shaft of the needle extends in the viewing direction of the endoscope, so that the range of the endoscope may possibly be intercepted by the shaft. In this case, it is necessary to change the course of the needle by bending the needle, and in addition, to change or increase the size of the bendable portion, thereby enabling the obstructive needle shaft to escape from the range of the endoscope. Since the curvature of the conventional needle is unchangeable, however, the impedimental needle shaft cannot be allowed to get away from the range.

In locally injecting the wall of a narrow duct, in contrast with this, the instrument cannot be caused squarely to approach a mucomembranous structure unless its bendable portion is reduced in size.

In the case of the catheter with its distal end easily bendable for cholangiography, its curved shape cannot be changed freely. This arrangement facilitates the insertion only when the catheter and the target tubular organism are in specific or restricted relative positions. If the catheter and the organism are not in these specific relative positions, however, the efficiency of insertion of the catheter cannot be improved. Thus, the catheter with the bendable distal end cannot be highly insertable under various conditions.

In inserting a catheter into the cystic duct, in general, the catheter is easily caught by a spiral fold (valve) in the duct, so that it cannot be inserted deep into the duct. In this case, the distal end of the catheter must be directed so that its curved shape can be frequently changed to clear the fold. In order to pass the spiral fold, moreover, the bendable portion is expected to have a measure of stiffness (rigidity). Since this requirement cannot be fulfilled according to the prior art described above, however, inserting the catheter into the cystic duct is a hard task. According to this arrangement, furthermore, the curved shape of the distal end of the catheter cannot be changed, so that a trocar having an unreasonably large diameter should be used to receive the bendable portion of the catheter. Thus, a large hole must be bored in the patient's body.

BRIEF SUMMARY OF THE INVENTION

The present invention has been contrived in consideration of these circumstances, and its object is to provide a surgical instrument capable of approaching a target region easily and safely in a proper direction.

In order to achieve the above object of the invention, there is provided a surgical instrument comprising: an elongate insert section adapted to be inserted into the body of a patient, the insert section including a distal end portion having a distal end opening and a proximal end portion located outside the patient's body; and an extracorporeal section connected to the proximal end portion and located outside the patient's body, the insert section including an elongate, substantially tubular, rigid sheath, the sheath having therein a channel ranging from the proximal end portion of the insert section to the distal end portion thereof, and a bendable portion attached to the distal end portion of the sheath and bendable in any desired direction, and the extracorporeal section including a fixing portion for fixing an elongate flexible insert member in any desired insertion position in the channel of the insert section and a bending section for optionally changing the curved shape of the bendable portion.

According to the present invention, the elongate flexible insert member is passed through the rigid sheath, and is fixed in any desired insertion position by means of a fixing portion of a handling-side control section. In this state, the shape of the bendable portion on the distal end side of the sheath can be easily changed by bending the bendable portion by means of the bending section. Thus, in treating an organism by means of the instrument, the curved shape of the bendable portion on the distal end side of the rigid sheath can be changed on the handling side so that the relative positions of the instrument and the target organism are corrected. In this manner, the instrument can be caused safely to approach the target region in a proper direction.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

FIG. 2 is a side view showing the distal end portion of the surgical instrument of the first embodiment;

FIG. 3 is a sectional view taken along line III—III of FIG. 2;

FIG. 4 is a side view of a string fixing portion according to the first embodiment;

FIG. 5A is a profile showing an unscrewed state of a tube fixing portion according to the first embodiment;

FIG. 5B is a profile showing a screwed state of the tube fixing portion of the first embodiment;

FIG. 9 is a diagram showing an outline of a surgical instrument according to a second embodiment of the invention;

FIG. 10A is a profile of the distal end portion of the surgical instrument of the second embodiment;

FIG. 10B is a profile showing a string fixing portion of the surgical instrument of the second embodiment;

FIG. 11A is a side view showing the distal end portion of the surgical instrument of the second embodiment;

FIG. 11B is a sectional view taken along line 11B—11B of FIG. 11A;

FIG. 12 is a profile of the handling side of the surgical instrument of the second embodiment;

FIG. 13A is a view showing the way the surgical instrument of the second embodiment is inserted in a narrow lumen;

FIG. 13B is a view showing a sharply bent state of a bendable portion of the surgical instrument of the second embodiment in the narrow lumen;

FIG. 16A is a side view schematically showing the general construction of a surgical instrument according to a third embodiment of the invention;

FIG. 16B is a sectional view taken along line 16B—16B of FIG. 16A;

FIG. 16C is a side view showing a curvature regulating slot of a handle section;

FIG. 18A is a profile showing an instrument fixing portion in the handle section of the applicator of the surgical instrument of the third embodiment;

FIG. 18B is a profile showing the way an additional instrument is fixed by means of the instrument fixing portion;

FIG. 19A is a side view showing a state in which a bendable portion of the applicator of the surgical instrument of the third embodiment is bent at a narrow angle;

FIG. 19B is a side view showing a state in which the bendable portion of the applicator is bent at a wide angle;

FIG. 24A is a profile showing the construction of a principal part of a surgical instrument according to a fifth embodiment of the invention;

FIG. 24B is a profile showing the construction of a principal part of a surgical instrument according to a sixth embodiment of the invention;

FIG. 24C is a cross-sectional view of a bendable portion of an applicator shown in FIG. 24B;

FIG. 24D is a profile showing the construction of a principal part of a surgical instrument according to a seventh embodiment of the invention;

FIG. 25A is a profile showing the internal construction of a bendable portion of a surgical instrument according to an eighth embodiment of the invention; and FIG. 25B is a sectional view taken along line 25B—25B of FIG. 25A.

DETAILED DESCRIPTION OF THE INVENTION

Preferred embodiments of the present invention will now be described with reference to the accompanying drawings.

Figure 1:
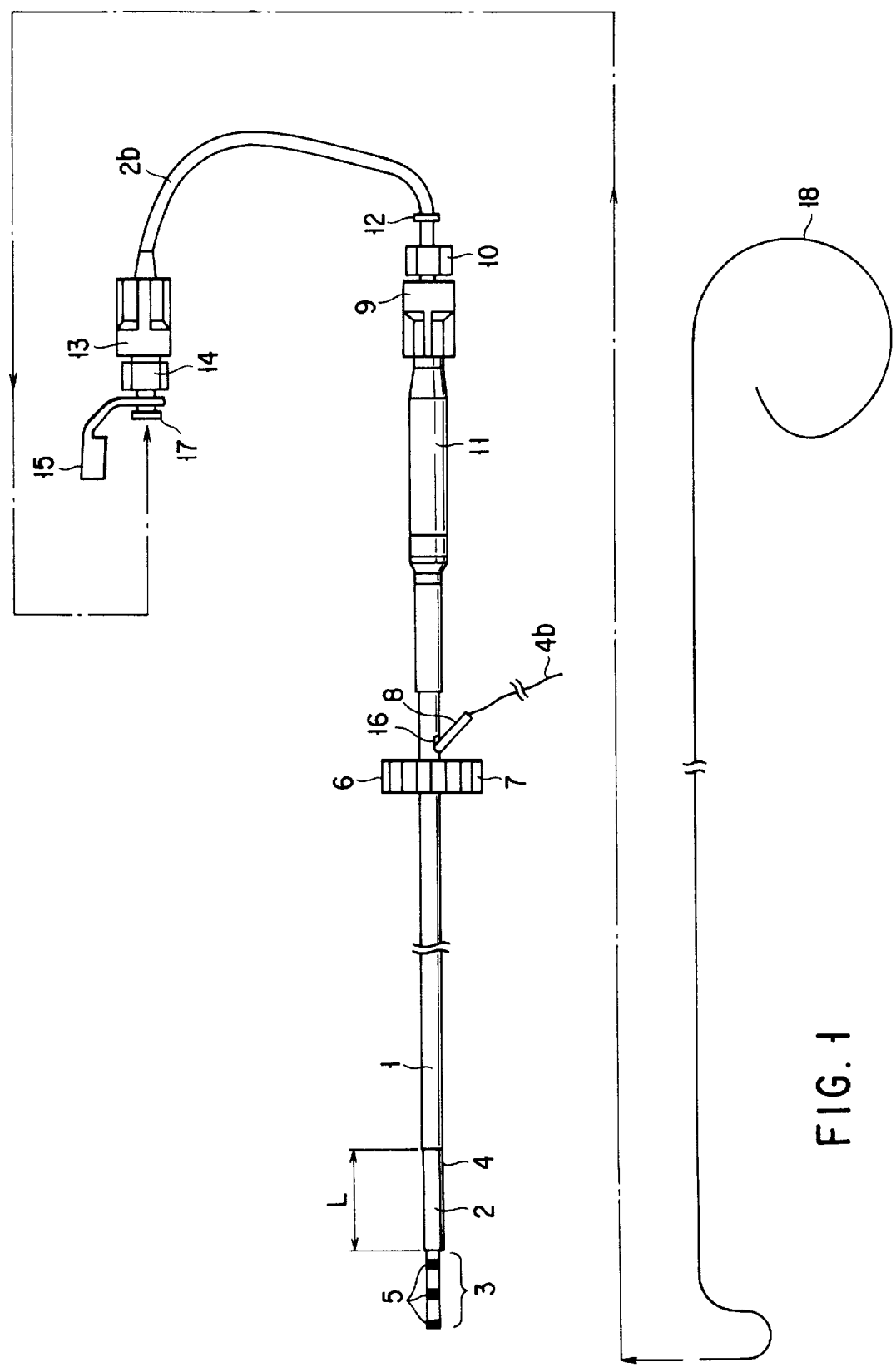
FIG. 1 is a diagram showing an outline of a surgical instrument according to a first embodiment of the present invention.

FIGS. 1 to 8B show a first embodiment of the invention. FIG. 1 is a diagram showing an outline of a surgical instrument according to the first embodiment. An insert section 1 of the surgical instrument is a rigid pipe. A tube 2 of e.g. Teflon, which is elastic enough to resist bending strain, is attached to the distal end of the insert section 1. A string 4, for use as curving means for curving the tube 2, is provided between the insert section 1 and the tube 2. The distal end portion of the string 4 is fixed to the tube 2.

Further, the tube 2 has an unbendable catheter inserting portion 3 of a certain length, which is located ahead of its string fixing portion. The inserting portion 3 is provided with markers 5 as indexes for the depth of insertion, which are arranged at regular intervals in the axial direction. Preferably, each interval ranges from 3 to 5 mm.

On the handling side of the insert section 1, the proximal end portion of the string 4 extends out of the insert section 1 through a hole 16. In FIG. 1, numeral 4b denotes a handling-side string portion that extends from the insert section 1 through the hole 16. That portion of the string which is situated near the hole 16 is protected by means of a string protector tube 8 lest it be cut by the outer peripheral edge of the hole 16. Further, the insert section 1 is provided with a string fixing portion 6 having slits 7, on the distal-end side of the hole 16.

A grip 11 and a first tube fixing portion 9 are provided on the handling side of the insert section 1. Further, the handling side of the first tube fixing portion 9 is connected with a second tube fixing portion 10. The fixing portion 10 is provided with a tube connector 12. A handling-side tube 2b extends from the connector 12.

The handling-side tube 2b has a length of about 50 to 150 mm. First and second guide wire fixing portions 13 and 14 are arranged at an end portion of the tube 2b. An injection connector 17 is provided on an end portion of the second guide wire fixing portion 14. The connector 17 serves as an injection portion from which a fluid is injected through the distal end of the catheter inserting portion 3. The connector 17 is fitted with a rubber cap 15 for preventing air from leaking from an internal duct. A guide wire 18, which will be described in detail later, is adapted to be inserted into the internal duct through the injection connector 17.

FIG. 2 shows the details of the distal end portion of the surgical instrument. The string 4 for bending operation is attached to that portion of the tube 2 which is situated at a distance from the distal end portion thereof. The string 4 is fixed in the following manner. A string fixing groove 19 is formed covering the entire circumference of the string fixing portion of the tube 2. The distal end portion of the string 4 that extends from between the insert section 1 and the tube 2 is fixedly wound at least once around the groove 19. Thus, the groove portion that is fixedly wound with the string 4 cannot axially slide with respect to the tube 2, so that the tube 2 can be bent in the manner indicated by broken line by pulling the string 4 to the handling side.

The string fixing groove 19 may be formed directly on the tube 2 or formed by putting a heat-shrinkable tube or the like on the tube 2 to create a stepped portion. Since the distal end portion of the string 4 can be fixed without boring the tube 2, there is no possibility of the fluid leaking from the tube 2 through its string fixing portion or trapping bubbles.

FIG. 3 is a sectional view taken along line III—III of FIG. 2. As shown in FIG. 3, two ribs 20 are arranged on the outer surface of the bendable portion of the tube 2, extending parallel to the axis of the tube 2. Thus, there is no possibility of the tube 2 buckling when its bendable portion is urged intensely to bend. The ribs 20 may be formed integrally with or independently of the tube 2. It is advisable to settle the positions and number of the ribs 20 depending on the characteristics of the tube 2 without being restricted by the conditions of the arrangement shown in FIG. 3.

FIG. 4 shows the details of the string fixing portion 6. The fixing portion 6, which is wing-shaped, is located just ahead of (or a little nearer to the distal end side than) the hole 16, on the axis of the insert section 1. Three slits 7 are arranged in each of two opposite wings of the fixing portion 6 so as to be symmetrical with respect to the axis of the insert section 1.

The handling-side string portion 4b can be fixed by being anchored to at least one of the slits 7 after it is pulled to obtain a desired curved shape, as mentioned before. Thus, the bendable portion of the tube 2 can be fixed to a certain curved shape. Each slit 7 is wedge-shaped. Preferably, the three slits 7 in each wing should have different widths so that a proper slit 7 can be selected on each occasion. The same function can be obtained with use of asymmetrically arranged slits 7 in the two wings or of only the slits in one wing. Further, the string fixing portion 6 may be situated remote from or close to the hole 16.

FIGS. 5A and 5B show the details of the first tube fixing portion 9. The grip 11 and the fixing portion 9 are fixed to each other by adhesive bonding. Alternatively, they may be fixed by means of screws. The first tube fixing portion 9 has a first thread portion 21 on its handling side. The thread portion 21 is in mesh with a second thread portion 22 that is formed on the second tube fixing portion 10. The first tube fixing portion 9 contains therein a fixing member 25, which has an inside diameter larger than that of the tube 2. The fixing member 25 is an elastic member formed of silicone rubber, for example.

In fixing the tube 2, the first and second thread portions 21 and 22 are tightened together by rotating the second tube fixing portion 10 with respect to the first tube fixing portion 9. As shown in FIG. 5B, moreover, the fixing member 25 is held between the respective abutting surfaces 24 and 23 of the first and second tube fixing portions 9 and 10 so that it is deformed, whereby the inside diameter of the fixing member 25 is reduced. Thus, the tube 2 can be fixed in a manner such that the inner surface of the fixing member 25 is pressed against it. This operation enables free adjustment of the length (length of the bendable portion designated by L in FIG. 1) of that portion of the tube 2 which projects from the distal end of the insert section 1.

Thus, in order to improve the operating efficiency of the catheter inserting portion 3, the length L of the bendable portion is optimized for each case. The efficiency of insertion of the inserting portion 3 can be improved by further bending the bendable portion. In addition, assembling operation can be carried out more efficiently because it requires neither bonding work for the bendable portion nor precise length adjustment.

For higher efficiency of insertion, moreover, the guide wire 18 is inserted through the injection connector 17. The wire 18 is fixed in the same manner as the tube 2 (so that the length of projection of the wire 18 from the distal end is set optionally).

The following is a description of an example of the way of using the surgical instrument.

Figure 6:
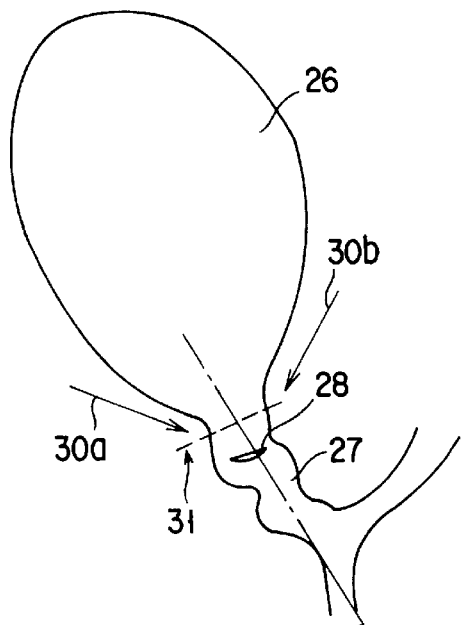
FIG. 6 is a view showing the way a contrast medium is injected for cholangiography according to the first embodiment.
Figure 7A:
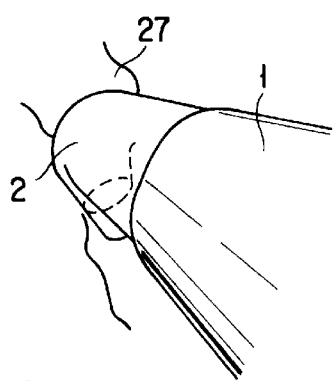
FIG. 7A is a perspective view showing a state such that an incision region is unrecognizable because it is intercepted by an insert section as the surgical instrument of the first embodiment is inserted into a cystic duct.
Figure 7B:
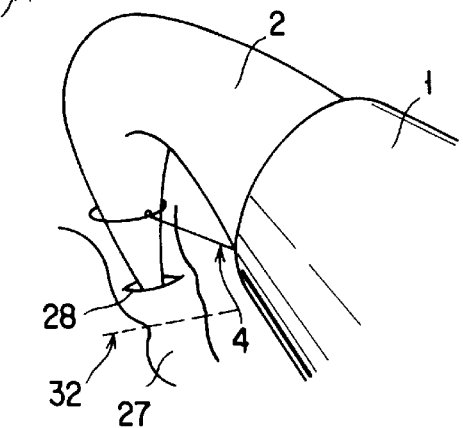
FIG. 7B is a perspective view showing a state such that a bendable portion is deformed to be lengthened as the surgical instrument of the first embodiment is inserted into the cystic duct.

FIGS. 6, 7A and 7B show the way a contrast medium is injected for cholangiography. First, a cystic duct 27 is incised so that the catheter inserting portion 3 can be inserted into the duct 27. An incision region 28 is incised by means of an instrument called an alligator forceps, which has a relatively long axis. In injecting the contrast medium, the cystic duct 27 must be previously clipped along a clipping line 31 on the gallbladder side of the incision region 28 by means of a clip for ligating a blood vessel or the like lest the medium flow into the gallbladder 26.

In this state, the catheter inserting portion 3 is inserted into the cystic duct 27 through the incision region 28. In many cases, as mentioned before, the instrument and the target structure (cystic duct) are then not in suitable relative positions for the operation of the instrument. In this state entire, it is very difficult to insert a catheter, since a central axis 29 of the cystic duct 27 is substantially deviated from approaching directions 30a and 30b (indicated by arrows in FIG. 6).

Thus, the insertion of the catheter inserting portion 3 through the incision region 28 can be facilitated by bending the distal end portion through the aforementioned operation to align the central axis 29 of the cystic duct 27 with the approaching direction 30a or 30b. Since this inserting operation can be carried out in the body cavity, the axis alignment does not require the instrument to be taken out of the body. Unlike a tube having a predetermined curved shape, moreover, the tube 2 can be operated without regard to the relative positions of the gallbladder and the instrument.

In the case where the object is approached in the direction shown in FIG. 7A, the insert section 1 and the tube 2 come within the range of an endoscope (not shown), depending on the length of the bendable portion, as shown in FIG. 7A, so that endoscopic images of the incision region 28 and the tube 2 cannot be recognized. In this case, it is necessary only that the insertion be tried again after changing the length of the bendable portion by operating the first and second tube fixing portions 9 and 10 in the aforesaid manner. Thus, the bendable portion shown in FIG. 7A is too short for the image recognition. Therefore, the insert section 1 and the tube 2 can be removed from the range of the endoscope by elongating the bendable portion so that it can be bent more sharply, as shown in FIG. 7B. By doing this, the catheter inserting portion 3 can be inserted safely and securely into the cystic duct 27.

Figure 8A:
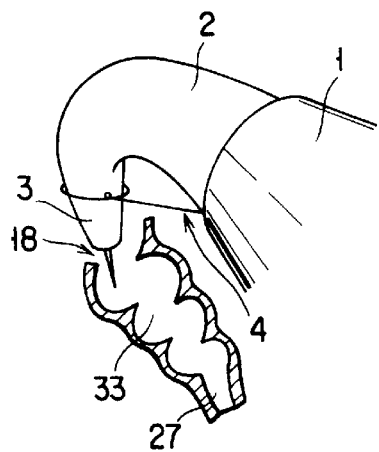
FIG. 8A is a perspective view showing the way the surgical instrument of the first embodiment is caused to approach a spiral fold of the cystic duct.
Figure 8B:
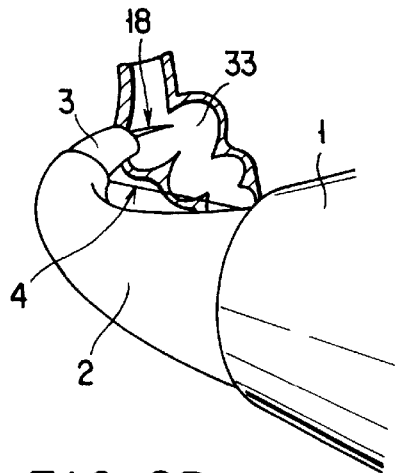
FIG. 8B is a perspective view showing the way the surgical instrument of the first embodiment is caused to approach the spiral fold of the cystic duct in a direction different from that of FIG. 8A.
Figure 14:
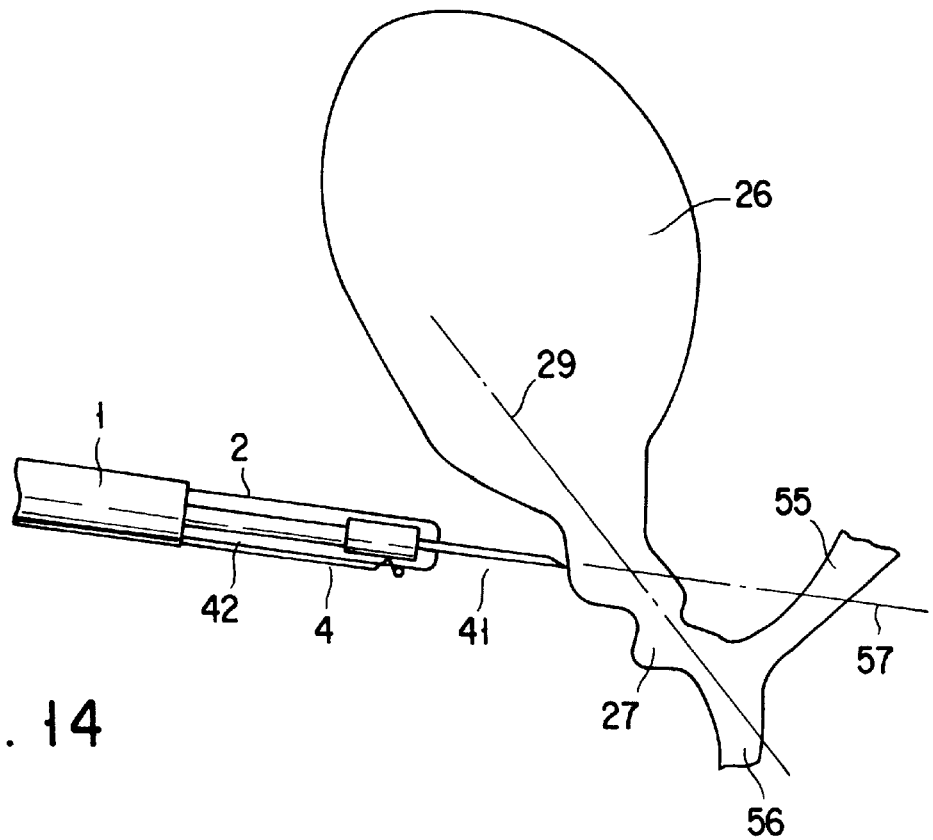
FIG. 14 is a view showing the way the contrast medium is injected for cholangiography according to the second embodiment.

In general, the cystic duct 27 has a valve and. a spiral fold 33 inside, as shown in FIG. 8A. If this spiral is sharp or if the duct is narrow inside, the catheter cannot be inserted with ease. In this case, the efficiency of insertion can be improved by using the guide wire 18. The wire 18 is caused in advance to project for a desired length from the catheter inserting portion 3 and be fixed by means of the first and second guide wire fixing portions 13 and 14. In this state, the guide wire 18 is first inserted into the cystic duct 27, and the catheter inserting portion 3 is then inserted into the duct 27 in a manner such that it is guided by the wire 18. As this is done, the direction of approach to the spiral fold 33, the bending angle, and the length of the bendable portion must be frequently adjusted, as shown in FIGS. 8A and 8B. Thus, the instrument according to the present embodiment can be regarded also as a useful guide wire pliers that facilitates the insertion of the guide wire 18.

The depth of insertion of the catheter inserting portion 3 into the cystic duct 27 can be easily grasped with reference to the markers 5. In injecting the contrast medium after the inserting portion 3 is inserted deeply enough into the duct 27, therefore, the inserting portion 3 and the duct 27 must be clipped together (along a half-clipping line 32 of FIG. 7B) lest the medium leak out through the gap between the inserting portion 3 the incision region 28. If the inserting portion 3 is clipped with a great force, at this time, its internal duct is constricted to prevent the flow of the contrast medium therein. Accordingly, the inserting portion 3 and the cystic duct 27 should be clipped with a light force (or half-clipped). The contrast medium is injected by means of a syringe that is attached directly to the injection connector 17. Before this is done, the guide wire 18 is removed from the connector 17.

FIGS. 9 to 15 show a second embodiment of the present invention. The following is a description of only differences between the first and second embodiments.

A needle 41 is attached to the distal end of a tube 2. A string 4 for bending operation is fixed to the distal end portion of the tube 2. An insert section 1 is fixed directly to a first tube fixing portion 9. As in the case of the first embodiment, a handling-side tube 2b extends from the handling side of the insert section 1. Further, the insert section 1 has a mount 43 and a slider 44 on its handling side and a lure-lock-shaped injection connector 45 on its terminal end portion. The slider 44 is used to cause the needle 41 to project and recede. The connector 45 can be connected directly with a syringe so that a fluid is injected through it.

FIG. 10A shows the details of the distal end portion of a surgical instrument according to the second embodiment. In this instrument, the root portion of the needle 41 is supported by means of a needle supporting portion 47 that has an outside diameter larger than that of the needle 41. The needle 41 can project and recede from the distal end of the tube 2. It is operated by moving the slider 44 in the direction of the arrow shown in FIG. 9. The maximum projection length of the needle 41 can be regulated, since the distal end portion of the tube 2 forms a distal-end constricted portion 48 that has a diameter smaller than the outside diameter of the needle supporting portion 47.

The handling side of the needle supporting portion 47 is connected to a liquid feed tube 42, and longitudinally moves together with the needle 41 in the tube 2. The tube 42 is connected to the slider 44 on the handling side. The terminal end of the tube 42 opens into the injection connector 45 shown in FIG. 9.

On the other hand, the distal end portion of the string 4 is fixed in the vicinity of the distal end portion of the tube 2. The string 4 is fixed in the following method. As shown in FIG. 10B, the distal end portion of the tube 2 has two string holes 2a1 and 2a2 that are large enough to allow the passage of the string 4. The string 4 is passed through the one hole 2a1 from the outside. Thereafter, the string 4 is passed again through the other hole 2a2 from the inside to the outside. Then, the string 4 is fixed to the tube 2 by means of a stopper 46 that is attached to its terminal end. The stopper 46 may be something like a grip or a knot made by passing the string 4 around the tube 2, for example. The stopper 46 can be formed more easily by knotting the end portion of the string 4 with the same effect. The distal end portion of the tube 2 can be bent in the manner indicated by broken line in FIG. 10A by pulling the handling-side string portion 4b to the handling side.

According to another fixing method for the string 4, as shown in FIG. 11A, a loop (string loop 58) of the string 4 is anchored to the distal end portion of the tube 2, and a string retainer ring 52 is provided so that the loop 58 cannot shift its position to the handling side. In this case, as shown in FIG. 11B, a string groove 53 should be formed on a part of the ring 52 so that the outside diameter of the ring 52 can be prevented from increasing by passing the string 4 through the groove 53.

FIG. 12 shows the details of the handling side of the surgical instrument. Grooves 49 are formed on the inner surface of the mount 43 that is connected to the handling-side tube 2b. The slider 44, which moves longitudinally in the mount 43, is provided on its outer surface with an O-ring mounting groove 50 and an O-ring 51 mounted therein. When the slider 44 slides, a clicking feeling is produced with the O-ring 51 of the slider 44 fitted in the groove 49 on the inner surface of the mount 43. At this time, the relative positions of the O-ring 51 and the groove 49 are adjusted so as to correspond to the stroke for projection and recession of the distal-end needle 41 from the distal end of the tube 2.

The following is a description of an example of the way of using the surgical instrument according to the present embodiment.

FIG. 13A shows a case in which the instrument according to the present embodiment is used in a narrow lumen, such as the gullet or intestinal tract. In the case where the instrument is located near the tangent to the surface of a mucous membrane as an object in the narrow lumen 54, as shown in FIG. 13A, it is very difficult to carry out local submucous injection by means of this instrument. In the case where the length of the bendable portion of the instrument is greater than the diameter of the duct in the organism, a satisfactory bending angle cannot be obtained, so that the instrument cannot be made to approach the surface of the mucous membrane in a correct direction (substantially perpendicular to the membrane surface).

In this case, the instrument can be thrust in the correct direction by sharply bending the bendable portion with a reduced length, that is, by increasing the bending angle, as shown in FIG. 13B.

The following is a description of the way the instrument is used for cholangiography, as in the first embodiment. In many cases, as mentioned before, the instrument and the target organism (cystic duct) are not in suitable relative positions for the operation of the instrument (e.g., state of FIG. 14). In thrusting the instrument in this state, it is difficult to locate the distal end of the needle 41 in the cystic duct 27, and in some cases, the thrust distal end of the needle 41 may penetrate the duct 27.

To avoid this, it is necessary to restrict the length of projection of the distal-end needle 41 or control the distal end of the needle 41 so as to be guided into the cystic duct 27 without regard to the length of projection of the needle 41 by aligning a central axis 57 of the needle 41 with the central axis 29 of the duct 27. As mentioned before, the length of projection of the needle 41 can be adjusted by means of the O-ring 51 on the slider 44.

Figure 15:
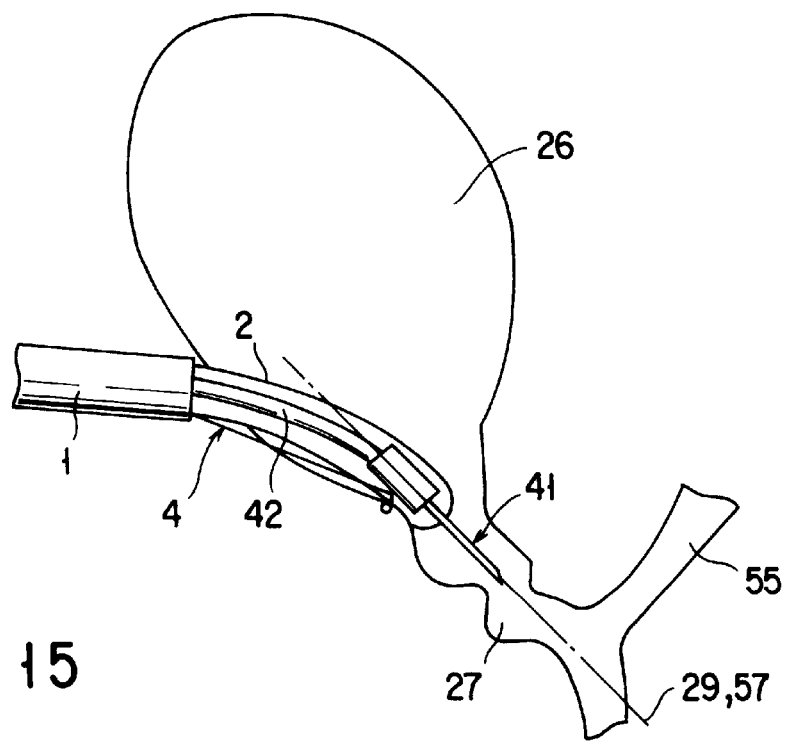
FIG. 15 is a view showing the way the surgical instrument of the second embodiment is inserted into the cystic duct.

By bending the distal end portion to align the respective central axes 29 and 57 of the cystic duct 27 and the needle 41, on the other hand, the distal end of the needle 41 can be securely guided into the duct 27 without being influenced by the depth of thrust of the needle 41, as shown in FIG. 15. Since a contrast medium can be injected by only thrusting the distal end of the needle 41, moreover, it is unnecessary to incise the cystic duct 27 or prevent the leakage of the medium by half-clipping after the insertion of the tube 2. Thus, the transfixing operation can be accomplished by means of the instrument according to the present embodiment alone without the aid of any other. instrument, so that manual work can be simplified substantially.

The contrast medium is injected by means of the syringe that is attached directly to the injection connector 45. Accordingly, the handling-side tube 2b is interposed between a syringe mounting portion and the insert section 1, so that an unexpected movement of the syringe cannot be transmitted to the needle 41 at the distal end of the insert section 1. Thus, the injecting operation can be carried out safely and securely.

This method is available for the case where the aforementioned spiral fold of the cystic duct 27 is deep, in particular. If the instrument is thrust into the cystic duct 27 with the central axis 29 of the duct 27 in alignment with the central axis 57 of the needle 41, the needle 41 can be safely run through the tissue that constitutes the spiral fold. Thus, the intended operation can be achieved without specially inserting a guide wire or catheter.

The following is a description of a method in which the instrument according to the present embodiment is used as a guide wire pliers. The guide wire is used in order to insert an operative endoscope, as well as to facilitate the aforesaid cholangiography.

The cholangiography is carried out as a treatment in cholecystectomy using a laparoscope. In this cholecystectomy, calculi in the gallbladder are enucleated together with the gallbladder. There may be some calculi in a common bile duct as well as in the gallbladder. In this case, the endoscope, especially a soft endoscope (soft scope), is inserted into the common bile duct, a basket forceps is inserted into a channel of the endoscope, and the calculi are enucleated.

The soft scope is inserted into the common bile duct through many routes. The guide wire pliers is good for use in any of these routes. The following is a description of the case of via a ductus cysticus route in the cystic duct.

1. The cystic duct 27 is incised.
2. The distal end of the catheter inserting portion 3 is inserted into the incision region 28, and the contrast medium is injected.
3. The guide wire 18 is caused to project slightly (for 2 to 10 mm) from the distal end of the catheter inserting portion 3.
4. When the guide wire 18 abuts against the spiral fold 33, the bending angle is changed, the insert section 1 is rotated, and the guide wire 18 is caused further to project. Then, the wire 18 is advanced. These operations are repeated as the wire 18 is passed along the spiral fold.

5. The distal end portion of guide wire 18 is advanced into the cystic duct 27 or into the duodenum via a duodenal papilla. The catheter inserting portion 3 may be advanced together with the wire 18.
6. The guide wire pliers is evulsed.
7. After the spiral fold 33 is dilated by means of a balloon dilator attached to the guide wire 18 and left on the fold 33, the dilator is evulsed.
8. The operative endoscope is guided by the guide wire 18 as it is inserted into the incision region 28. In doing this, the endoscope may be assisted in insertion by being grasped by means of an endoscope holding forceps.
9. The endoscope is inserted into the common bile duct via the spiral fold.
10. The guide wire 18 is evulsed, and calculi are extracted.

In some cases, Step 7 need not be carried out.

FIGS. 16A to 22F show a third embodiment of the present invention. FIG. 16A schematically shows the general construction of a surgical instrument 61 according to the present embodiment. The surgical instrument 61 is provided with an insertion guide applicator 62 and a flexible elongate instrument (elongate insert member) 63 to be inserted into the applicator 62. The additional instrument 63 that is inserted into the applicator 62 may be an injection needle 63A shown in FIGS. 16A and 19A, a laser probe 63B shown in FIG. 19B, or a contrast catheter 63D shown in FIG. 21, for example. Further, the applicator 62 may be combined with a bioptome 63C shown in FIG. 23, clip, electrocautery using high-frequency current, snare, heat probe, etc., for use treatment instruments, an ultrasonic probe, Doppler rheometer, slender endoscopes, etc., for use as diagnostic apparatuses, and a light guide cable as a light source.

The applicator 62 according to the present embodiment is provided with an insert section (rigid cylindrical member) 64 formed of a rigid pipe. A bendable portion 65 is attached to the distal end of the insert section 64.

Figure 17A:
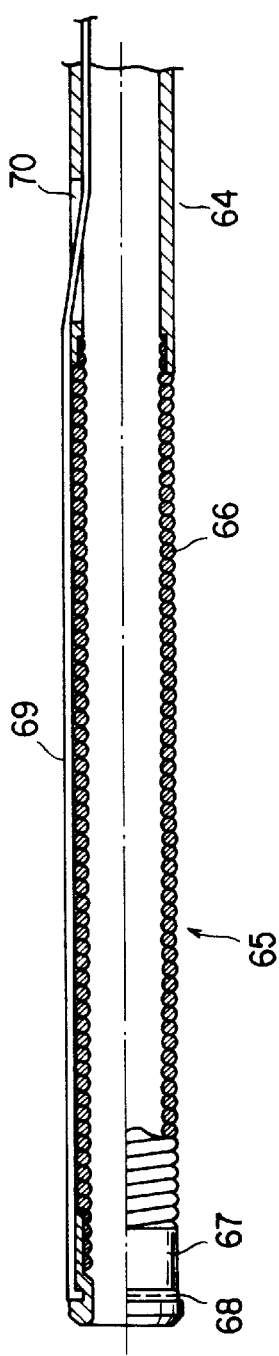
FIG. 17A is a profile showing the distal end portion of an applicator of the surgical instrument of the third embodiment.

As shown in FIG. 17A, the bendable portion 65 is composed of a closely-wound coil sheath 66. A rigid distal-end ring 67 is fixed to the distal end portion of the coil sheath 66 by welding. A wire fixing groove 68 is formed covering the whole outer peripheral surface of the ring 67. Further, the distal end portion of a traction wire 69 is fixed in a coil in the groove 68.

Figure 17B:
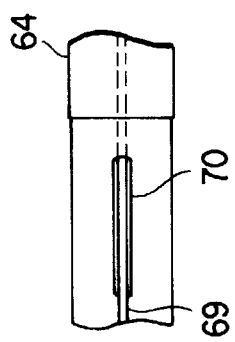
FIG. 17B is a plan view showing a principal part of a wire inlet hole in the outer peripheral surface of the distal end portion of the applicator.

Likewise, the proximal end portion of the coil. sheath 66 is fixed to the distal end portion of the rigid pipe of the insert section 64 by welding. As shown in FIG. 17B, moreover, an elongate wire inlet hole 70 is formed on the rigid pipe of the insert section 64, extending along the central axis of the insert section 64, in a position a little nearer to the handling side than the welded portion of the sheath 66. The traction wire 69 is located in contact with the outer surface of the bendable portion 65, and is led into the insert section 64 through the hole 70. The hole 70 is in the form of a slot, which enables the wire 69 to be pulled without resistance and prevents the wire 69 from being deformed by an undue force when it is pulled.

Figure 17C:
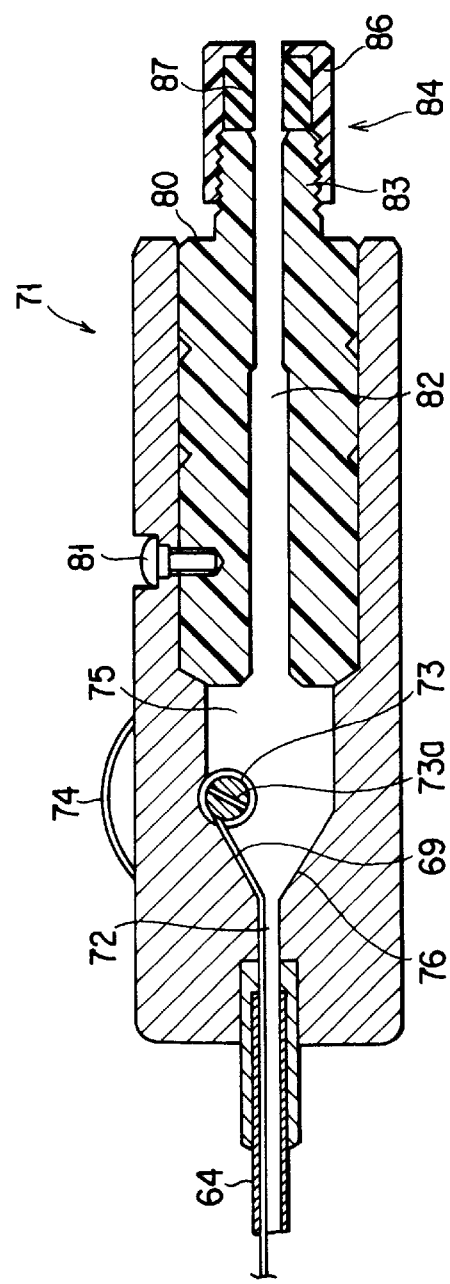
FIG. 17C is a profile showing the handle section on the handling side of the applicator.

A handle section (control section) 71 on the handling side is attached to the proximal end portion of the insert section 64. As shown in FIG. 17C, the handle section 71 has therein a duct 72 that communicates with the rigid pipe of the insert section 64. The traction wire 69 in the insert section 64 is then guided into the duct 72 of the handle section 71 on the handling side.

Further, a wire take-up shaft 73 for winding up the traction wire 69 is rotatably supported in the handle section 71. As shown in FIG. 17C, the shaft 73 is situated with an offset from the center of the handle section 71.

As shown in FIG. 16B, the two opposite end portions of the wire take-up shaft 73 penetrate the handle section 71 and project individually from the opposite sides of the section 71. Further, circular knobs (bending section) 74 for bending the bendable portion 65 are connected individually to the opposite projecting portions of the shaft 73. These two circular knobs 74 are arranged bisymmetrically on either side of the handle section 71.

A through hole 73a is bored through the center of the wire take-up shaft 73. The proximal end portion of the traction wire 69 is fixed to the shaft 73 in a manner such that the wire 69 is wound the shaft 73 with its proximal end portion passed through the hole 73a. The shaft 73 is rotated by turning one of the knobs 74, and the traction wire 69 is pulled toward the handling side by winding the wire 69 around the shaft 73. As this is done, the bendable portion 65 is bent.

Moreover, a large-diameter portion 75 having a large inside diameter is defined in that portion of the duct 72 in the handle section 71 in which the wire take-up shaft 73 is mounted. A smooth taper surface 76 is formed between the large-diameter portion 75 and a small-diameter portion of the duct 72 nearer to the distal end side. When the wire 69 is pulled, it is taken up by the shaft 73 in the large-diameter portion 75. Thus, the wire 69 wound on the shaft 73 can be prevented from bending so sharply that it produces traction resistance.

One of the knobs 74 is fitted with a knob fixing screw 77 for fixing it to the handle section 71. Further, the handle section 71 is formed having a curvature regulating slot 78 that substantially covers half the circumference of that portion against which the tip of the screw 77 abuts. The tip portion of the screw 77 is regulated so that it can move only in the regulating slot 78. Thus, the range of movement of the knob 74, that is, the pull of the traction wire 69, is restricted by the slot 78 so that the bendable portion 65 cannot be bent beyond a certain degree of curvature. In FIG. 16A, solid and imaginary lines indicate an unbent state and a maximally bent state of the bendable portion 65, respectively.

A tubular insertion guide member 80 is attached to the terminal end portion of the handle section 71 and fixed by means of a fixing screw 81. The additional instrument 63 is guided by the guide member 80 as it is inserted into the applicator 62. A lumen 82 is formed in the axis portion of the guide member 80. The lumen 82 has an inside diameter larger than the outside diameter of the instrument 63. The instrument 63 is inserted into the applicator 62 through an opening of the lumen 82 of the guide member 80. The instrument 63 in the applicator 62 is designed to be guided along the smooth taper surface 76, from the large-diameter portion 75 in the handle section 71 toward the small-diameter portion of the duct 72 on the distal end side. Accordingly, the instrument 63 in the applicator 62 can be smoothly passed from the large-diameter portion 75 to the small-diameter portion of the duct 72 on the distal end side. Further, the instrument 63 can be led out from the duct 72 in the handle section 71 via the interior of the rigid pipe of the insert section 64 and the bendable portion 65 at the distal end of the insert section 64 and through the opening of the distal-end ring 67. In the example shown in FIG. 16A, the injection needle 63A is inserted as the instrument 63 into the applicator 62 to be combined therewith.

A protrusion 83 is formed on one end portion of the insertion guide member 80, projecting outward from the handle section 71. The protrusion 83 is provided with an instrument fixing member (fixing portion) 84 for fixing the additional instrument 63 in any desired position in the applicator 62. An external thread portion 85 for mounting the fixing member 84 is formed on the outer peripheral surface of the protrusion 83 of the guide member 80.

As shown in FIG. 18A, moreover, the instrument fixing member 84 is provided with a fixing cap 86, substantially in the form of a bottomed cylinder, and a rubber ring 87 as an elastic member in the cap 86. A bottom portion of the cap 86 is formed having a center hole 86a through which the instrument 63 is inserted. On the open end side of the fixing cap 86, the internal peripheral surface of a cylindrical portion of the cap 86 is formed having a tapped hole portion 86b, which mates with the external thread portion 85 of the insertion guide member 80.

The rubber ring 87 has an instrument passage hole 87a, the inside diameter of which is a little larger than the outside diameter of the instrument 63. As shown in FIG. 18A, the ring 87 is kept in its natural state without being clamped when the tapped hole portion 86b of the fixing cap 86 of the instrument fixing member 84 is not deeply in engagement with the external thread portion 85 of the insertion. guide member 80. In this state, the instrument 63 is kept slidable without being clamped by anything when it is inserted into the lumen 82 of the guide member 80 through the holes 86a and 87a.

As the fixing cap 86 is tightened after the instrument 63 is inserted into the lumen 82 of the insertion guide member 80 through the through holes 86a and 87a of the instrument fixing member 84, as shown in FIG. 18B, the rubber ring 87 therein is deformed to clamp the inserted portion of the instrument 63. In this manner, the instrument 63 is fixed and sealed.

The following is a description of the operation of this structure. The surgical instrument 61 according to the present embodiment is used in a manner such that any of various instruments 63 is combined with the applicator 62, depending on the method of treatment. In combining the applicator 62 with the additional instrument 63, e.g., the injection needle 63A shown in FIG. 16A, the elongate needle 63A is passed through the applicator 62. When the needle 63A is inserted into any desired insertion position, it is fixed to the applicator 62 by means of the instrument fixing member 84 of the handle section 71 on the handling side.

In the case of the surgical instrument 61 according to the present embodiment, the wire take-up shaft 73 is rotated by turning one of the knobs 74 of the handle section 71, and the traction wire 69 is pulled to the handling side to bend the bendable portion 65 by winding the wire 69 around the shaft 73. By adjusting the rotation of the knob 74, the curved shape of the bendable portion 65 can be easily changed between the unbent state indicated by solid line in FIG. 16A and the maximally bent state indicated by imaginary line.

In the case where the plane of a mucomembranous structure 91, an object of local injection, is substantially parallel to the central axis of the surgical instrument 61 according to the present embodiment, as shown in FIG. 19A, the bendable portion 65 of the applicator 62 is bent with the applicator 62 kept combined with the injection needle 63A. Thus, a needle tip 92 at the distal end of the needle 63A can be caused to approach the mucomembranous structure 91 at a thrust angle θ such that it faces the plane of the structure 91 substantially squarely.

After an affected part 91a on the plane of the mucomembranous structure 91 is bulged with a medical solution locally injected through the injection needle 63A, it is excised by means of the laser probe 63B that is combined with the applicator 62, as shown in FIG. 19B. In doing this, the bendable portion 65 of the applicator 62 is bent with the applicator 62 and the probe 63B kept combined. If the bendable portion 65 is then bent to a higher degree than in the state of FIG. 19A, a laser beam can be applied to the inner region of the bulged affected part 91a through the distal end portion of the laser probe 63B to excise it, as shown in FIG. 19B.

Further, the range of movement of the distal end portion of the knob fixing screw 77 is regulated by means of the curvature regulating slot 78 of the handle section 71. When one of the knobs 74 is turned, therefore, the pull of the traction wire 69 is restricted by the slot 78, so that the bendable portion 65 cannot be bent beyond a certain degree of curvature. The laser probe 63B is so fragile that it breaks if it is bent too sharply. Since the slot 78 serves securely to prevent the probe 63B from being bent beyond its maximum degree of curvature, however, the probe 63B can avoid being damaged.

Thus, in treating the organism by means of the surgical instrument 61 according to the present embodiment, the instrument 61 can be caused safely to approach the target region in a proper direction by changing the curved shape of the bendable portion 65 at the distal end of the insert section 64 on the handling side so that the relative positions of the instrument 61 and the organism are corrected.

Figure 20:
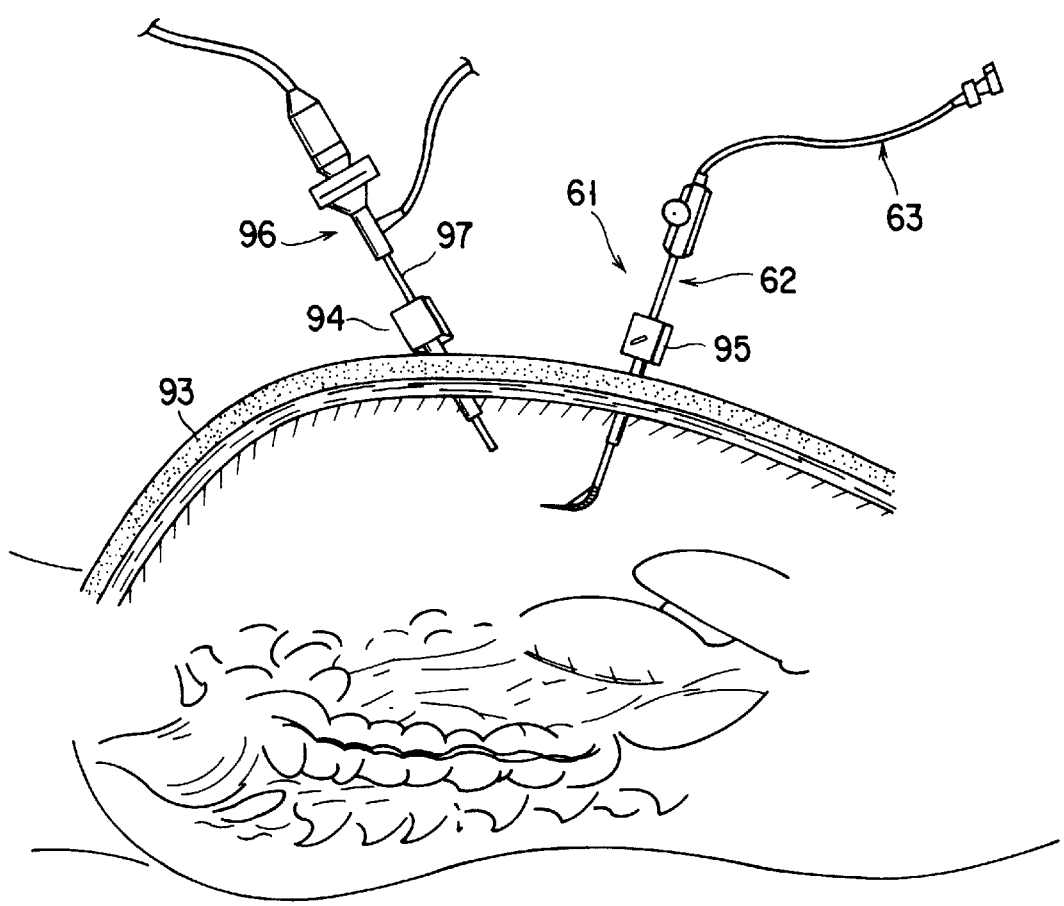
FIG. 20 is a view schematically showing the way the applicator of the surgical instrument of the third embodiment used in a laparoscopic operation.

The following is a description of an example of actual application of the surgical instrument 61 according to the present embodiment arranged in this manner. FIG. 20 shows the way of using the surgical instrument 61 in a laparoscopic operation. In FIG. 20, numeral 93 denotes an abdominal region of a patient's body. The abdominal region 93 is transfixed with two trocars 94 and 95. An insert section 97 of a laparoscope 96 is passed through the one trocar 94, and the surgical instrument 61 according to the present embodiment through the other trocar 95.

Figure 21:
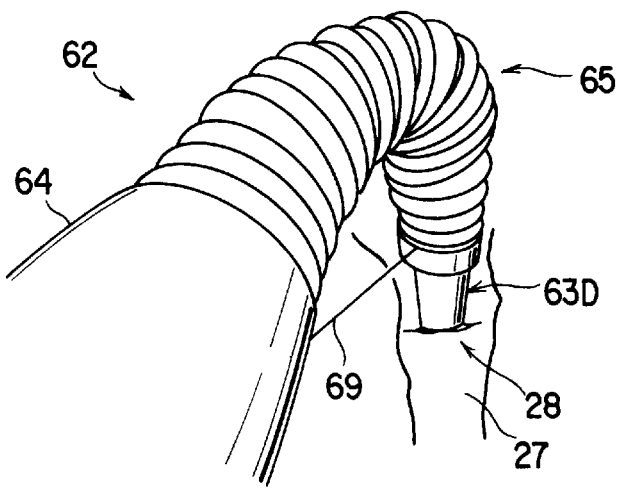
FIG. 21 is a perspective view of a principal part showing a bent state of the bendable portion of the applicator of the surgical instrument of the third embodiment.

In the surgical instrument 61 according to the present embodiment used in this operation, as shown in FIG. 21, the applicator 62 and the contrast catheter 63D are used in combination for cholangiography. The steps of procedure for the cholangiography have been described before in connection with the first embodiment (see FIGS. 6, 7A and 7B).

In the surgical instrument 61 according to the present embodiment, the bendable portion 65 of the applicator 62 is composed of the closely-wound coil sheath 66, so that it can be given a measure of stiffness (rigidity). In inserting the instrument 61 into the cystic duct 27, therefore, the bendable portion 65 can be waved with an appropriate force as it passes along the spiral fold 33.

FIGS. 22A to 22F illustrate the way of excising only a lesion 102 in a mucomembranous structure 101 in a patient's body. In general, a physiological saline solution or the like is locally injected into an area around the lesion 102 that remains in the structure 101 so that the lesion 102 can be excised with the structure 101 lifted (or separated) in the saline solution.

Further, FIGS. 22A to 22F show the case in which the tissue (lesion 102 remaining in the mucomembranous structure 101) to be excised lies substantially parallel to the central axis of the surgical instrument 61. In the case where the plane of the mucomembranous structure 101, as the object of local injection, is thus substantially parallel to the central axis of the instrument 61 according to the present embodiment, the bendable portion 65 of the applicator 62 is bent with the applicator 62 and the injection needle 63A kept combined together. By doing this, the needle tip 92 of the needle 63A can be caused to approach the plane of the mucomembranous structure 101 substantially squarely.

The following is a description of a method of treatment in which a laser knife 63E and a solution of ICG (indocyanine green) are combined to be used as means for excising the mucomembranous structure 101. The laser knife 63E used in this method is a semiconductor laser having a wavelength of about 805 nm. The absorption spectrum of the ICG solution in an organism is substantially equal to the wavelength of the diode laser. Accordingly, the organism that contains the ICG solution can absorb a laser beam more efficiently than one that does not.

The following is a description of steps of procedure for excising the mucomembranous structure 101.

Figure 22A:
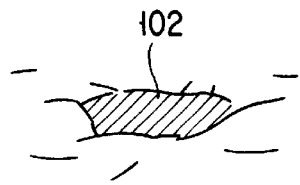
FIGS. 22A to 22F are views for illustrating steps of procedure for excising a mucomembranous structure by means of the surgical instrument of the third embodiment.

(a) First, the lesion 102 remaining in the mucomembranous structure 101 is recognized by means of the laparoscope 96, as shown in FIG. 22A.

Figure 22D:
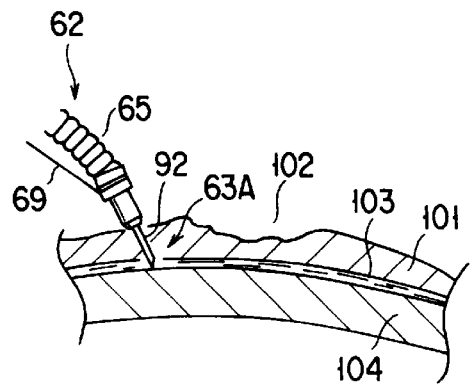
Figure 22B:
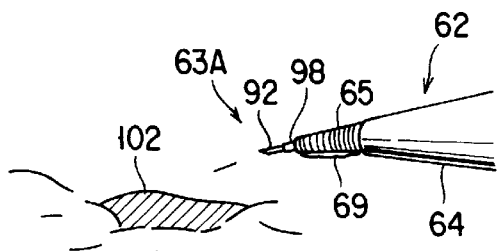

(b) Then, the injection needle 63A is combined with the applicator 62, and comes within the range of the laparoscope 96, as shown in FIG. 22B. The needle 63A approaches substantially in the direction of the tangent to the plane of the mucomembranous structure 101.

Figure 22E:
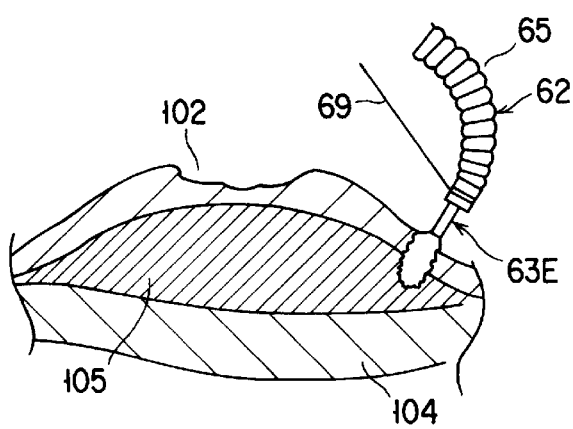
Figure 22C:
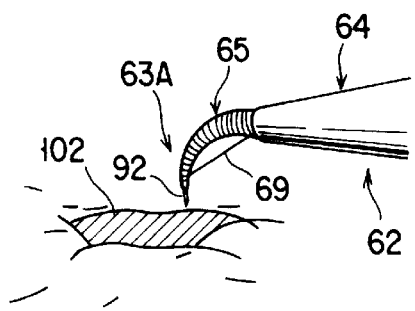

(c) As shown in FIG. 22C, moreover, the bendable portion 65 of the applicator 62 is deformed into a desired curved shape, with the tip 92 of the injection needle 63A projecting from the distal end of a sheath 98 of the needle 63A, in the range of the laparoscope 96.

(d) In this state, the tip 92 of the injection needle 63A is thrust into the area around the lesion 102, as shown in FIG. 22D. The distal end of the tip 92 of the needle 63A is guided to a submucosa 103 under the mucomembranous structure 101, and the ICG solution is injected into the submucosa 103. In doing this, it is confirmed that the lesion 102 is bulged satisfactorily. As shown in FIG. 22E, at this time, an ICG solution 105 exists under the mucomembranous structure 101, so that the structure 101 is separated or kept at a good distance from a muscular tunic 104 that underlies the submucosa 103.

(e) Then, the injection needle 63A is disengaged from the applicator 62 and replaced with a laser probe of the laser knife 63E. Subsequently, the curvature of the bendable portion 65 of the applicator 62 is suitably adjusted as the distal end of the laser probe of the laser knife 63E is held against the area around the lesion 102 to incise it, as shown in FIG. 22E. Since the ICG under the mucomembranous structure 101 then absorbs the laser, the influence of the laser cannot be easily exerted on the muscular tunic 104 under the submucosa 103 that is injected with the ICG.

Figure 22F:
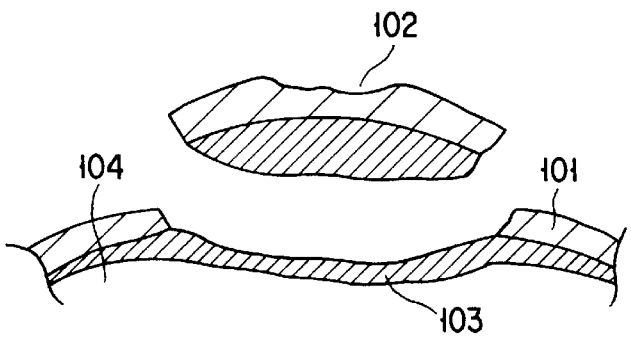

(f) Thus, the submucosa 103 can be securely incised without damaging the muscular tunic 104, as shown in FIG. 22F, and the lesion 102 in the mucomembranous structure 101 can be excised en bloc.

This method is applicable in particular to excision of the mucous membranes of digestive tracts, such as the stomach, intestines, etc. It is characterized principally in that the mucomembranous structure 101 can be securely excised along the submucosa 103 without entailing bleeding or substantial injuries by heat. As compared with the conventional method in which an electrocautery is used for excision, therefore, the method of the present invention has its highest merit in that it can avoid the possibility of injuring the muscular tunic 104 or unexpected perforation.

According to the present embodiment, the diode laser is combined with the ICG solution. It is to be understood, however, that the method of the invention can produce the same effects only if the wavelength of the laser is substantially equal to the absorption spectrum of the solution combined with the laser.

Accordingly, the following effects can be obtained from the arrangement described above. When the surgical instrument 61 according to the present embodiment is used, the instrument 63, such as the elongate injection needle 63A, is passed through applicator 62. Thus, any of various instruments 63 can be used in combination with the applicator 62, depending on the method of treatment.

In combining the applicator 62 and the instrument 63, the elongate injection needle 63A is passed through the applicator 62. When the needle 63A is inserted into any desired insertion position, it is fixed to the applicator 62 by means of the instrument fixing member 84 of the handle section 71 on the handling side. In this state, the shape of the bendable portion 65 on the distal end side of the insert section 64 can be easily changed by turning one of the two knobs 74 of the handle section 71 to bend the bendable portion 65. Thus, in treating the organism by means of the surgical instrument 61 according to the present embodiment, the curved shape of the bendable portion 65 can be easily changed between the unbent state indicated by solid line in FIG. 16A and the maximally bent state indicated by imaginary line by adjusting the rotation of the knob 74. In consequence, the relative positions of the instrument 61 and the target organism can be corrected with ease, so that the instrument 61 can be caused safely to approach the target region in a proper direction.

According to the present embodiment, moreover, the bendable portion 65 of the applicator 62 is composed of the closely-wound coil sheath 66, so that it can be given a measure of stiffness (rigidity). Even when the bendable portion 65 is bent repeatedly, therefore, it can be prevented from becoming highly susceptible to bending.

In the case where the bendable portion 65 is composed of the closely-wound coil sheath 66, as in the present embodiment, moreover, the instrument 63 can be smoothly inserted into the applicator 62 without being caught by a coil portion of the coil sheath 66. Unlike a roughly-wound coil sheath, the coil sheath 66 can prevent the additional instrument 63 from meeting with resistance or being shaved at its distal end as it passes through the bendable portion 65.

Further, the handle section 71 is provided with the two knobs 74, and the bendable portion 65 is bent by turning one of the knobs 74 to rotate the wire take-up shaft 73. Accordingly, the bendable portion 65 of the applicator 62 can be bent one-handed, thus enjoying improved operating efficiency.

Figure 23:
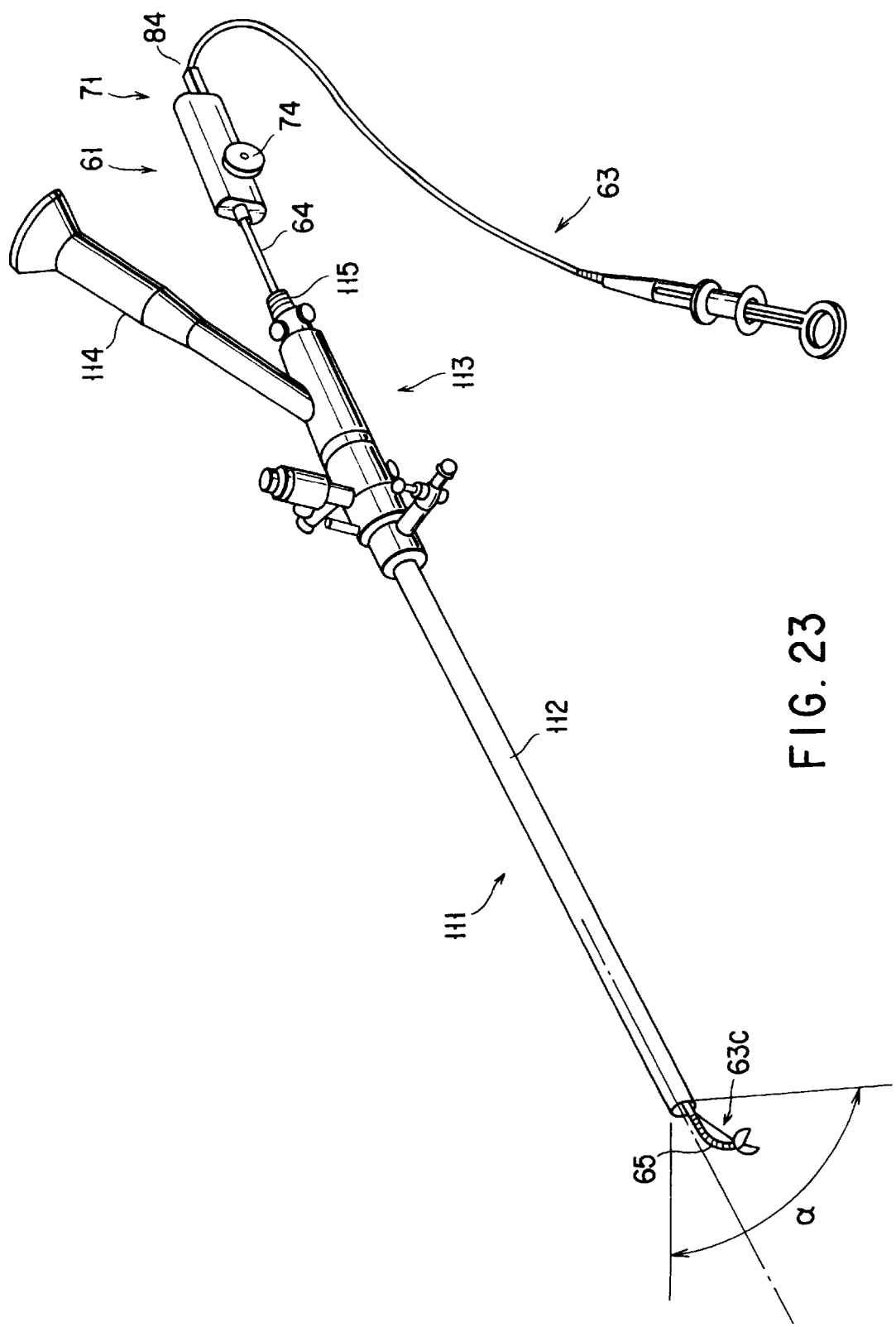
FIG. 23 is a perspective view showing an outline of a surgical instrument according to a fourth embodiment of the invention.

FIG. 23 shows a fourth embodiment of the present invention. In the present embodiment, the surgical instrument 61 according to the third embodiment (see FIGS. 16A to 22F) is used in combination with a rigid scope 111. In this case, the surgical instrument 61 is inserted in the scope 111 when it is actually used.

The rigid scope 111 according to the present embodiment is used to approach the renal pelvis, ureter, urinary bladder, urethra, etc., for example. The scope 111 is provided with a rigid sheath 112 in the form of a straight pipe, which constitutes an insert section to be inserted into the patient's body. An extracorporeal handling-side end section 113 is attached to the proximal end portion of the sheath 112.

An eyepiece section 114 protrudes from the handling-side end section 113, and an instrument inserting portion 115 is attached to the end section 113. Defined in the sheath 112, moreover, is a channel through which the instrument 61 or the like is passed. The instrument 61 is inserted into the channel of the sheath 112 through an opening of the inserting portion 115 of the end section 113. Thus, the instrument 61 can be used under observation through the scope 111.

Further, the surgical instrument 61 according to the present embodiment is an example of a combination of the applicator 62 and the bioptome 63C. The bioptome 63C is attached to the applicator 62 in advance, and in this state, it is inserted into the channel of the scope 111.

The view angle (α) of the scope 111 is so wide that the bioptome 63C of the surgical instrument 61 can come within the range of the scope 111 even when the bendable portion 65 of the applicator 62 is bent.

Thus, the above combination is serviceable because the bioptome 63C according to the present embodiment cannot satisfactorily extract a target organism unless it is caused to approach the organism squarely, in particular.

FIG. 24A shows a fifth embodiment of the present invention. According to the present embodiment, the arrangement of the bendable portion 65 of the applicator 62 of the surgical instrument 61 according to the third embodiment (see FIGS. 16A to 22F) is modified in the following manner.

In the present embodiment, the closely-wound coil sheath 66 that constitutes the bendable portion 65 of the applicator 62 is covered by a thin, soft cover member 121 (e.g., latex rubber).

Generally, in the case where the bendable portion 65 of the applicator 62 is composed of the closely-wound coil sheath 66, gaps are created in the coil portion of the sheath 66 when the bendable portion 65 is bent, especially when it is bent sharply, and the organism may possibly be caught by these gaps. According to the present embodiment, however, the thin, soft cover member 121 that covers the coil sheath 66 can prevent the gaps in the coil portion from catching the organism.

FIGS. 24B and 24C show a sixth embodiment of the present invention. According to the present embodiment, the arrangement of the bendable portion 65 of the applicator 62 of the surgical instrument 61 according to the third embodiment (see FIGS. 16A to 22F) is modified in the following manner.

In the present embodiment, the bendable portion 65 of the applicator 62 is composed of a tube 131 such as a Teflon tube, which is resilient against bending stress, and six core bars 132 embedded integrally in the tube 131. The core bars 132 are arranged parallel to the central axis of the tube 131.

According to the present embodiment, the six core bars 132, embedded integrally in the tube 131, can prevent the tube 131 from becoming more susceptible to bending as the bendable portion 65 of the applicator 62 is bent repeatedly or from being buckled by excessive bending.

FIG. 24D shows a seventh embodiment of the present invention. According to the present embodiment, the arrangement of the bendable portion 65 of the applicator 62 of the surgical instrument 61 according to the third embodiment (see FIGS. 16A to 22F) is modified in the following manner.

In the present embodiment, the bendable portion 65 of the applicator 62 is integrally molded by embedding a roughly-wound coil sheath 142 in a flexible resin tube 141.

Thus, according to the present embodiment, the additional instrument 63 can be smoothly inserted into the applicator 62, and an organism can be prevented from being caught by the outer surface of the coil sheath 142.

FIGS. 25A and 25B show an eighth embodiment of the present invention. According to the present embodiment, the arrangement of the applicator 62 of the surgical instrument 61 according to the third embodiment (see FIGS. 16A to 22F) is modified in the following manner.

In the present embodiment, an insert section 152 of the applicator 62 is composed of an elongate flexible resin tube 151, as shown in FIG. 25A. As shown in FIG. 25B, moreover, the resin tube 151 is formed having a large-diameter lumen 153, through which the additional instrument 63 is passed, and a small-diameter lumen 154 for the traction wire 69.

Wedge-shaped slits 155 are arranged only on the bending side of the distal end portion of the flexible resin tube 151. This portion in which the slits 155 are arranged side by side constitutes a bendable portion 156 that is bendable in one direction only.

The distal end portion of the traction wire 69 is fixed at the distal end of the lumen 154 for the wire 69. By pulling the wire 69 on the handling side, the bendable portion 156 can be bent without drawing out the wire 69 from the flexible resin tube 151, as indicated by imaginary line in FIG. 25A.

It is to be understood that the present invention is not limited to the embodiments described above, and that various changes and modifications may be effected therein by one skilled in the art without departing from the scope or spirit of the invention.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical instrument comprising:

an elongate insert section adapted to be inserted into the body of a patient, the insert section including a distal end portion having a distal end opening and a proximal end portion adapted to be located outside the patient's body; and an extracorporeal section connected to the proximal end portion and adapted to be located outside the patient's body, the insert section including an elongate, substantially tubular, rigid sheath, the sheath having therein a channel ranging from the proximal end portion of the insert section to the distal end portion thereof, and a bendable portion attached to the distal end portion of the sheath and bendable in any desired direction, said bendable portion including a flexible tubular body, and the extracorporeal section including a fixing portion for fixing an elongate flexible insert member in any desired insertion position in the channel of the insert section, and a bending section for optionally changing the curved shape of said bendable portion, said bending section including a control wire having one end fixed to a distal end portion of the tubular body and wire pulling means for pulling the control wire, thereby bending the bendable portion of the insert section.

2. The instrument according to claim 1, wherein said fixing portion includes sealing means for maintaining an airtightness of an interior of the channel of the insert section with the insert member in the desired insertion position in the channel.

3. The instrument according to claim 2, wherein:

said fixing portion includes a ring-shaped elastic member, having a through hole with a diameter larger than an outside diameter of the insert member such that the insert member is passed through the through hole, and a screw member capable of elastically deforming the elastic member between an initial state in which the elastic member is kept substantially in a natural state and a compressed state in which the elastic member is pressed inward from outside so that the insert member passed through the through hole is fixed immovably; and said sealing means comprises the elastic member elastically deformed into the compressed state.

4. The instrument according to claim 1, wherein said flexible tubular body comprises a coil sheath capable of maintaining a substantially rectilinear initial shape in a natural state and adapted to be deformed into any desired curved shape when pulled by means of the wire pulling means, and said flexible tubular body is restored from the desired curved shape to the initial shape by means of an elastic force of the coil sheath after the bendable portion is bent into the desired curved shape by the wire pulling means.

5. The instrument according to claim 4, wherein said coil sheath comprises a closely-wound coil.

6. The instrument according to claim 4, wherein said bendable portion comprises the coil sheath and a soft sheetlike covering member covering an outer surface of the coil sheath.

7. The instrument according to claim 4, wherein said coil sheath is integrally molded in one niece with a tube formed of a flexible material.

8. The instrument according to claim 4, wherein said coil sheath is formed having a coating layer of a low-friction material on an inner surface thereof.

9. The instrument according to claim 1, wherein:
said flexible tubular body of said bendable portion includes a flexible tube and slits extending substantially at right angles to a central axis of the tube, the slits being arranged side by side along the central axis of the tube, and the tube having a wire passage lumen on the open end side of the slits; and
said control wire passes through the wire passage lumen.

10. The instrument according to claim 1, wherein said extracorporeal section further includes a grip portion, and said bending section includes a knob, rotatably mounted on the grip portion and capable of pulling the control wire, and knob fixing means capable of rotating the knob, thereby pulling the control wire, and adapted to fix a rotational position of the knob, thereby settling the curved shape of the bendable portion.

11. The instrument according to claim 10, wherein said grip portion includes a rotation regulating slot for regulating the rotation of the knob, and said bending section includes means for regulating a curvature of the bendable portion within a range of the rotation regulating slot.

12. The instrument according to claim 1, wherein the extracorporeal section further includes an infecting portion from which a fluid is injected, in a proximal end portion of the elongate flexible insert member, and a soft connecting tube for connecting a proximal end portion of the rigid sheath and the injecting portion.

13. The instrument according to claim 1, wherein:
the insert section includes an injection needle for injecting a medical solution into a submucosal layer beneath a lesion of a mucous membrane, thereby separating a mucomembranous structure from a musclaris propriae; and
the instrument further comprises:
a semiconductor laser for incising the mucous membrane around the lesion, separated from the musclaris propriae, the semiconductor laser having substantially a same wavelength as an absorption spectrum of the injected medical solution; and
a removing device arranged to remove the lesion excised by the semiconductor laser.

14. The instrument according to claim 3, wherein said medical solution comprises ICG (indocyanine green).

15. A surgical instrument comprising:
an elongate insert section adapted to be inserted into the body of a patient, the insert section including a distal end portion having a distal end opening and a proximal end portion adapted to be located outside the patient's body; and
an extracorporeal section connected to the proximal end portion and adapted to be located outside-the patient's body,
the insert section including an elongate, substantially tubular, rigid sheath, the sheath having therein a channel ranging from the proximal end portion of the insert section to the distal end portion thereof, and a bendable portion attached to the distal end portion of the sheath and bendable in any desired direction, and
the extracorporeal section including a fixing portion for fixing an elongate flexible insert member in any desired insertion position in the channel of the insert section and a bending section for optionally changing the curved shape of said bendable portion,
wherein:
said rigid sheath has a distal end opening,
said fixing portion includes a projection length adjusting portion for optionally changing a length of a projection of the insert member projecting outward from the distal end opening of the sheath, and
said bending section includes means for bending the projection of the insert member projecting from the distal end opening of the sheath, and a fixing portion for fixing the bendable portion of the insert member in a given curved shape.

16. The instrument according to claim 15, wherein said insert member comprises a tube having a passage adapted to enable a fluid to be injected into the patient's body, and said extracorporeal section includes an injecting portion for injecting the fluid into the tube.

17. The instrument according to claim 16, further comprising a wire-shaped guide member adapted to be inserted into the tube through the injecting portion and a guide member fixing portion connected to a proximal end portion of the tube and adapted to fix the guide member in any desired position such that the guide member projects from the distal end portion of the insert member.

18. The instrument according to claim 16 wherein said tube includes an injection needle connected to a distal end portion thereof.

19. The instrument according to claim 18, wherein said needle has a large-diameter portion thicker than a distal end portion of the needle, at a junction with the tube, said tube moves along a central axis of the sheath, between a first position in which the needle projects from the distal end opening of the sheath and a second position in which the needle is hidden in the sheath, said sheath has an abutting portion in a peripheral edge region of the distal end opening thereof, the abutting portion having a diameter smaller than that of the large-diameter portion of the needle and serving to restrict the projection of the needle as the needle moves toward the first position, and said extracorporeal section includes means for fixing the needle in any desired position between the first and second positions.

20. The instrument according to claim 15, wherein said bending section includes a string for pulling the projection of the insert member to bend the projection, the string having a distal end portion fixed to the distal end portion of the insert member and a rear end portion guided to the extracorporeal section side via an interior of the sheath.

21. The instrument according to claim 20, wherein the distal end portion of said insert member has a ring-shaped string fixing groove formed covering an entire circumference of an outer peripheral surface thereof, and the distal end portion of said string has a string loop fixedly wound on the groove, the string loop having an inside diameter substantially equal to an outside diameter of the groove.

22. The instrument according to claim 20, wherein the distal end portion of said insert member has a ring-shaped projection formed covering an entire circumference of an outer peripheral surface thereof, and the distal end portion of said string has a string loop fixedly wound on a part of the distal end portion of the insert member nearer to the distal end than the projection.

23. The instrument according to claim 20, wherein said sheath includes a fixing portion for fixing the rear end portion of the string, the fixing portion having at least one slit with a width nearly equal to an outside diameter of the string, and said fixing portion fixes the projection in any desired curved shape in a manner such that the rear end portion of the string is anchored to the slit with the projection of the insert member bent by being pulled by means of the string.

24. The instrument according to claim 15, wherein said bendable portion of said insert member includes a rib protruding from an outer peripheral surface thereof and extending parallel to a central axis of the insert member.

* * * * *